(12) United States Patent
Stapper et al.

(10) Patent No.: US 7,220,876 B2
(45) Date of Patent: May 22, 2007

(54) ARYLCYCLOALKYL DERIVATIVES HAVING BRANCHED SIDE CHAINS, PROCESSES FOR THEIR PREPARATION AND THEIR USE AS PHARMACEUTICALS

(75) Inventors: Christian Stapper, Mainz (DE); Heiner Glombik, Hofheim (DE); Eugen Falk, Frankfurt (DE); Jochen Goerlitzer, Frankfurt am Main (DE); Dirk Gretzke, Frankfurt (DE); Stefanie Keil, Hofheim (DE); Hans-Ludwig Schaefer, Hochheim (DE); Wolfgang Wendler, Selters (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 435 days.

(21) Appl. No.: 10/789,323

(22) Filed: Feb. 27, 2004

(65) Prior Publication Data

US 2004/0209873 A1 Oct. 21, 2004

Related U.S. Application Data

(60) Provisional application No. 60/487,575, filed on Jul. 15, 2003.

(30) Foreign Application Priority Data

Feb. 27, 2003 (DE) .................. 103 08 352

(51) Int. Cl.
C07C 229/00 (2006.01)
C07C 261/00 (2006.01)
C07C 63/00 (2006.01)

(52) U.S. Cl. .............. 560/19; 562/405; 562/433; 562/442; 562/451; 560/24; 560/37

(58) Field of Classification Search ............. 562/405, 562/433, 439, 442, 452, 465; 560/8, 19, 560/24, 27, 29

See application file for complete search history.

(56) References Cited

U.S. PATENT DOCUMENTS

| | | | |
|---|---|---|---|
| 6,221,633 B1 | 4/2001 | Ertl | |
| 6,221,897 B1 | 4/2001 | Frick | |
| 6,245,744 B1 | 6/2001 | Frick | |
| 6,277,831 B1 | 8/2001 | Frick | |
| 6,342,512 B1 | 1/2002 | Kirsch | |
| 6,525,069 B1 | 2/2003 | Ko et al. | |

FOREIGN PATENT DOCUMENTS

| | | |
|---|---|---|
| DE | 38 73 992 | 12/1988 |
| EP | 0 293 880 A1 * | 12/1988 |
| EP | 0 462 884 A1 | 12/2001 |
| JP | 2002201171 | 7/2002 |
| JP | 20002201127 | 7/2002 |
| WO | WO 94/18183 | 8/1994 |
| WO | WO 94/18184 | 8/1994 |
| WO | WO 96/38428 | 12/1996 |
| WO | WO 97/26265 | 7/1997 |
| WO | WO 97/41097 | 11/1997 |
| WO | WO 98/08871 | 3/1998 |
| WO | WO 98/19998 | 5/1998 |
| WO | WO 99/03861 | 1/1999 |
| WO | WO 99/15525 | 4/1999 |
| WO | WO 99/61431 | 12/1999 |
| WO | WO 99/62871 | 12/1999 |
| WO | WO 99/62872 | 12/1999 |
| WO | WO 99/67278 | 12/1999 |
| WO | WO 99/67279 | 12/1999 |
| WO | WO 00/40569 | 7/2000 |
| WO | WO 00/63208 | 10/2000 |
| WO | WO 00/64876 | 11/2000 |

(Continued)

OTHER PUBLICATIONS

Asakawa A et al., Cocaine-Amphetamine-Regulated Transcript Influences Energy Metabolism Anxiety and Gastric Emptying in Mice, Hormone and Metabolic Research; vol. 33(9); 2001; pp. 554-558.

(Continued)

Primary Examiner—Thurman K. Page
Assistant Examiner—Yevgeny Valenrod
(74) Attorney, Agent, or Firm—Barbara E. Kurys

(57) ABSTRACT

Arylcycloalkyl derivatives having branched side chains, processes for their preparation and their use as pharmaceuticals The invention relates to arylcycloalkyl derivatives having branched side chains and to their physiologically acceptable salts and physiologically functional derivatives.

What is described are compounds of the formula I,

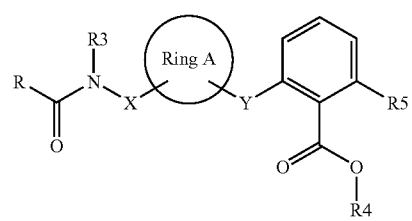

in which the radicals are as defined, and their physiologically acceptable salts and processes for their preparations. The compounds are suitable for the treatment and/or prevention of disorders of fatty acid metabolism and glucose utilization disorders as well as of disorders in which insulin resistence is involved.

15 Claims, No Drawings

FOREIGN PATENT DOCUMENTS

| | | |
|---|---|---|
| WO | WO 00/64888 | 11/2000 |
| WO | WO 00/66585 | 11/2000 |
| WO | WO 00/71549 | 11/2000 |
| WO | WO 00/78312 A1 | 12/2000 |
| WO | WO 01/04146 A2 | 1/2001 |
| WO | WO 01/09111 A1 | 2/2001 |
| WO | WO 01/21602 A1 | 3/2001 |
| WO | WO 01/40169 A1 | 6/2001 |
| WO | WO 01/40171 A1 | 6/2001 |
| WO | WO 01/72290 A2 | 10/2001 |
| WO | WO 01/81327 A1 | 11/2001 |
| WO | WO 01/83451 | 11/2001 |
| WO | WO 01/85695 A1 | 11/2001 |
| WO | WO 01/91752 A1 | 12/2001 |
| WO | WO 01/94300 | 12/2001 |
| WO | WO 02/38541 A1 | 5/2002 |
| WO | WO 02/46146 A1 | 6/2002 |
| WO | WO 02/50027 | 6/2002 |
| WO | WO 02/064549 A1 | 8/2002 |
| WO | WO 02/096864 | 12/2002 |
| WO | WO 03/004458 A1 | 1/2003 |
| WO | WO 03/020269 | 3/2003 |
| WO | WO 03/040174 A2 | 5/2003 |
| WO | WO 03/066581 A1 | 8/2003 |
| WO | WO 03/084922 | 10/2003 |
| WO | WO 03/084923 | 10/2003 |
| WO | WO 03/104188 | 12/2003 |

OTHER PUBLICATIONS

Berger Joel et al., The Mechanisms of Action of PPARs, Annul. Rev. Med.; vol. 53; 2002; pp. 409-435.

Fruchart Jean-Charles et al., PPARs, Metabolic Disease and Atherosclerosis, Pharmacological Research; vol. 44, No. 5; 2001' pp. 345-352.

Kersten Sander et al., Roles of PPARs in Health and Disease, Nature; vol. 405; May 25, 2000; pp. 421-424.

Kliewer Steven A et al., Peroxisome Proliferator-Activated Receptors: From Genes to Physiology, Recent Prog. Horm Res.; vol. 56; 2001; pp. 239-263.

Lee Daniel W et al., Leptin agonists as a potential approach to the treatment of obesity, Drugs of the Future; vol. 26(9); 2001; pp. 873-881.

Motojima Kiyoto, Peroxisome Proliferator-Activated Receptor (PPAR): Structure, Mechanisms of Activation and Diverse Functions, Cell Structure and Function; vol. 18; 1993; pp. 267-277.

Okada Hiroshi et al., Synthesis and Antitumor Activities of Prodrugs of Benzoylphenylureas, Chem. Pharm. Bull.; vol. 42(1); 1994; pp. 57-61.

Pineda Torra Ines et al., Peroxisome Proliferator-activated Receptors: from Transcriptional Control to Clinical Practice, Curr. Opin. Lipidol; vol. 12; 2001; pp. 245-254.

Pineda Torra Ines et al., Peroxisome proliferator-activated receptor alpha in metabolic disease, Inflammation, atherosclerosis and aging, Curr. Opin. Lipidol; vol. 10; 1999; pp. 151-159.

Vidal-Puig A et al., Regulation of PPAR y Gene Expression by Nutrition and Obesity in Rodents, J. Clin. Invest.; vol. 97, No. 11, 1996; pp. 2553-2561.

Wilson Timothy M. et al., The PPARs; From Orphan Receptors to Drug Discovery, Journal of Medicinal Chemistry; vol. 43, No. 4; 2000; pp. 527-550.

Zunft H,. J. F. et al., Carob Pulp Preparation for Treatment of Hypercholesterolemia, Advances in Natural Therapy; vol. 18, No. 5; Sep.-Oct. 2001; pp. 230-236.

* cited by examiner

SEQUENCE LISTING

<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: Binding Site of Yeast Transcription Factor GAL4

<400> SEQUENCE: 1
cggagtactg tcctccgag                                                   19

<210> SEQ ID NO 2
<211> LENGTH: 19
<212> TYPE: DNA
<213> ORGANISM: Artificial
<220> FEATURE:
<223> OTHER INFORMATION: Binding Site of Yeast Transcription Factor GAL4

<400> SEQUENCE: 2
ctcggaggac agtactccg                                                   19

ARYLCYCLOALKYL DERIVATIVES HAVING BRANCHED SIDE CHAINS, PROCESSES FOR THEIR PREPARATION AND THEIR USE AS PHARMACEUTICALS

DESCRIPTION

The invention relates to arylcycloalkyl derivatives having branched side chains and to their physiologically acceptable salts and physiologically functional derivatives.

Compounds of a similar structure have already been described in the prior art for the treatment of hyperlipidemia and diabetes (WO 2000/64876).

The invention was based on the object of providing compounds which permit therapeutically utilizable modulation of lipid and/or carbohydrate metabolism and are thus suitable for the prevention and/or treatment of diseases such as type 2 diabetes and atherosclerosis and the diverse sequelae thereof.

A series of compounds which modulate the activity of PPA receptors has surprisingly been found. The compounds are suitable in particular for activating PPARalpha and PPARgamma, it being possible for the extent of the relative activation to vary depending on the compounds.

Accordingly, the invention relates to compounds of the formula I

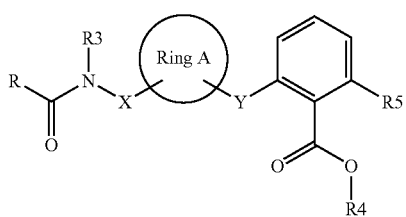

wherein
ring A is (C3-C8)-cycloalkanediyl or (C3-C8)-cycloalkenediyl, wherein one or more carbon atoms in said (C3-C8)-cycloalkanediyl and (C3-C8)-cycloalkenediyl groups are optionally replaced by oxygen atoms;
R is NR1R2 or OR1, (C6-C10)-aryl or (C5-C12)-heteroaryl, wherein said (C5-C12)-heteroaryl group contains one, two or three identical or different heteroatoms selected from the group consisting of N, O and S;
R1, R2 are each independently H, (C1-C6)-alkyl, (C3-C8)-cycloalkyl or (C6-C10)-aryl, wherein said (C6-C10)-aryl is optionally substituted by F, Cl or (C1-C4)-alkyl;
R3 is (C3-C6)-cycloalkyl or (C1-C10)-alkyl, wherein each group is optionally substituted by phenyl, pyridyl, morpholinyl or (C3-C6)-cycloalkyl, and wherein said phenyl substituent is optionally substituted by chlorine or (C1-C4)-alkyl;
X is (C1-C6)-alkanediyl, wherein one or more carbon atoms therein are optionally replaced by oxygen atoms;
Y is (C1-C6)-alkanediyl, wherein one or more carbon atoms therein are optionally replaced by oxygen atoms;
R4 is H or (C1-C4)-alkyl;
R5 is (C1-C4)-alkyl;
and pharmaceutically acceptable salts thereof.

Preference is given to compounds of the formula I wherein substituents X and Y are linked to ring A in position 1,3 (X-ring A-Y).

Preference is furthermore given to compounds of the formula I wherein:
ring A is (C3-C8)-cycloalkane-1,3-diyl or (C3-C8)-cycloalkene-1,3-diyl;
R is NR1R2 or (C6-C10)-aryl;
R1, R2 are each independently H, (C1-C6)-alkyl, (C3-C8)-cycloalkyl or (C6-C10)-aryl, wherein said (C6-C10)-aryl group is optionally substituted by F, Cl or (C1-C4)-alkyl;
R3 is (C3-C6)-cycloalkyl or (C1-C8)-alkyl, wherein each group is optionally substituted by phenyl, pyridyl, morpholinyl, (C3-C6)-cycloalkyl, and wherein said phenyl substituent is optionally substituted by chlorine or methyl;
X is (C1-C3)-alkanediyl, wherein one carbon atom therein is optionally replaced by an oxygen atom;
Y is (C1-C3)-alkanediyl, wherein the carbon atom adjacent to ring A in said (C1-C3)-alkanediyl group is optionally replaced by an oxygen atom;
R4 is H;
R5 is methyl;
and pharmaceutically acceptable salts thereof.

Particular preference is given to compounds of the formula I wherein:
ring A is cyclohexane-1,3-diyl;
R is NR1R2 or phenyl;
R1 is H;
R2 is (C1-C6)-alkyl, cyclohexyl or phenyl, wherein said phenyl group is optionally substituted by F, Cl or (C1-C4)-alkyl;
R3 is (C3-C6)-cycloalkyl or (C1-C8)-alkyl, each of which is optionally substituted by phenyl, pyridyl, morpholinyl, cyclopropyl, cyclopentyl, cyclohexyl, and wherein said phenyl substituent is optionally substituted by chlorine or methyl;
X is O—CH$_2$—CH$_2$;
Y is OCH$_2$;
R4 is H;
R5 is methyl;
and pharmaceutically acceptable salts thereof.

Very particular preference is given to compounds of the formula I wherein:
ring A is cyclohexane-1,3-diyl;
R is NR1R2 or phenyl;
R1 is H;
R2 is (C1-C4)-alkyl, cyclohexyl or phenyl, wherein said phenyl group is optionally substituted by F, Cl or methyl;
R3 is (C3-C6)-cycloalkyl or (C1-C8)-alkyl, each of which is optionally substituted by phenyl, pyridyl, morpholinyl, cyclopropyl, cyclopentyl or cyclohexyl, and wherein said phenyl substituent is optionally substituted by chlorine or methyl;
X is O—CH$_2$—CH$_2$;
Y is OCH$_2$;
R4 is H;
R5 is methyl;
and pharmaceutically acceptable salts thereof.

The link to ring A can be either cis or trans and is preferably cis.

This invention also encompasses all combinations of preferred aspects of the invention described herein.

The alkyl radicals in the substituents R1, R2, R3, R4 and R5 may be either straight-chain or branched.

Aryl means an aromatic carbocyclic mono- or bicyclic ring system which comprises 6 to 10 atoms in the ring or rings.

Heteroaryl is a mono- or bicyclic aromatic ring system having 4 to 11 ring members, in which at least one atom in the ring system is a heteroatom from the series N, O and S.

The compounds of the formula I comprise at least two centers of asymmetry and may comprise more in addition. The compounds of the formula I may therefore exist in the form of their racemates, racemic mixtures, pure enantiomers, diastereomers and mixtures of diastereomers. The present invention encompasses all these isomeric forms of the compounds of the formula I. These isomeric forms can be obtained by known methods even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

This invention relates further to the use of compounds of the formula I and their pharmaceutical compositions as PPAR ligands. The PPAR ligands of the invention are suitable as modulators of PPAR activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta, which are encoded by different genes (Peroxisome proliferator-activated receptor (PPAR): structure, mechanisms of activation and diverse functions: Motojima K, Cell Struct Funct. 1993 October; 18(5): 267-77).

Two variants of PPARgamma exist, PPARgamma$_1$ and gamma$_2$, which are the result of alternative use of promoters and differential mRNA splicing (Vidal-Puig et al. J. Clin. Invest., 97:2553-2561, 1996). Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effect and pathophysiology, see: Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63.

The present invention relates to compounds of the formula I suitable for modulating the activity of PPARs, especially the activity of PPARalpha and PPARgamma. Depending on the modulation profile, the compounds of the formula I are suitable for the treatment, control and prophylaxis of the indications described hereinafter, and for a number of other pharmaceutical applications connected thereto (see, for example, Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63; Jean-Charles Fruchart, Bart Staels and Patrick Duriez: PPARS, Metabolic Disease and Arteriosclerosis, Pharmacological Research, Vol. 44, No. 5, 345-52; 2001; Sander Kersten, Beatrice Desvergne & Walter Wahli: Roles of PPARs in health and disease, NATURE, VOL 405, 25 May 2000; 421-4; Ines Pineda Torra, Giulia Chinetti, Caroline Duval, Jean-Charles Fruchart and Bart Staels: Peroxisome proliferator-activated receptors: from transcriptional control to clinical practice, Curr Opin Lipidol 12: 2001, 245-254).

Compounds of this type are particularly suitable for the treatment and/or prevention of 1.—disorders of fatty acid metabolism and glucose utilization disorders
   disorders in which insulin resistance is involved
2. Diabetes mellitus, especially type 2 diabetes, including the prevention of the sequelae associated therewith. Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentrations
   low ApoA lipoprotein concentrations
   high LDL cholesterol concentrations
   small dense LDL cholesterol particles
   high ApoB lipoprotein concentrations
4. Various other conditions which may be associated with the metabolic syndrome, such as:
   obesity (excess weight), including central obesity
   thromboses, hypercoagulable and prothrombotic states (arterial and venous)
   high blood pressure
   heart failure such as, for example (but not restricted thereto), following myocardial infarction, hypertensive heart disease or cardiomyopathy
5. Other disorders or conditions in which inflammatory reactions or cell differentiation may for example be involved are:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   pancreatitis
   other inflammatory states
   retinopathy
   adipose cell tumors
   lipomatous carcinomas such as, for example, liposarcomas
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
   acute and chronic myeloproliferative disorders and lymphomas
   angiogenesis
   neurodegenerative disorders
   Alzheimer's disease
   multiple sclerosis
   Parkinson's disease
   erythemato-squamous dermatoses such as, for example, psoriasis
   acne vulgaris
   other skin disorders and dermatological conditions which are modulated by PPAR
   eczemas and neurodermitis
   dermatitis such as, for example, seborrheic dermatitis or photodermatitis
   keratitis and keratoses such as, for example, seborrheic keratoses, senile keratoses, actinic keratosis, photo-induced keratoses or keratosis follicularis
   keloids and keloid prophylaxis
   warts, including condylomata or condylomata acuminata
   human papilloma viral (HPV) infections such as, for example, venereal papillomata, viral warts such as, for example, molluscum contagiosum, leukoplakia
   papular dermatoses such as, for example, Lichen planus
   skin cancer such as, for example, basal-cell carcinomas, melanomas or cutaneous T-cell lymphomas
   localized benign epidermal tumors such as, for example, keratoderma, epidermal naevi
   chilblains
   high blood pressure
   syndrome X
   polycystic ovary syndrome (PCOS)
   asthma
   osteoarthritis
   lupus erythematosus (LE) or inflammatory rheumatic disorders such as, for example, rheumatoid arthritis
   vasculitis
   wasting (cachexia)
   gout
   ischemia/reperfusion syndrome
   acute respiratory distress syndrome (ARDS)

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type 11 diabetes and arteriosclerosis and the diverse sequalae thereof.

Combinations with Other Medicaments

The compounds of the invention can be administered alone or in combination with one or more further pharmacologically active substances which have, for example, favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:

Antidiabetics

Suitable antidiabetics are disclosed for example in the Rote Liste 2001, chapter 12 or in the USP Dictionary of USAN and International Drug Names, US Pharmacopeia, Rockville 2001. Antidiabetics include all insulins and insulin derivatives such as, for example, Lantus® (see www-.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S.

The orally effective hypoglycemic active ingredients include, preferably, sulfonylureas, biguanides, meglitinides, oxadiazolidinediones, thiazolidinediones, glucosidase inhibitors, glucagon antagonists, GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188)

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, metformin.

In a further embodiment, the compounds of the formula I are administered in combination with a meglitinide such as, for example, repaglinide.

In one embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S,4S)-4-fluoro-1-[[(2-hydroxy-1,1-dimethylethyl)amino]-acetyl]pyrrolidine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid reabsorption inhibitor (see, for example, U.S. Pat. No. 6,245,744, U.S. Pat. No. 6,221,897, U.S. Pat. No. 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höechst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a mixed PPAR alpha/gamma agonist such as, for example, AZ 242 (Tesaglitazar, (S)-3-(4-[2-(4-methanesulfonyloxyphenyl)ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein(a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl )thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dex-amphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention. The activity of the compounds was tested as follows:

Determination of EC50 Values of PPAR Agonists in the Cellular PPARalpha Assay

Principle

The potency of substances which bind to human PPARalpha and activate in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is integrated in the genome of the cell line. There is only little expression of the luciferase reporter gene without addition of a PPARalpha ligand if fatty acid-depleted fetal calf serum (cs-FCS) is used in the assay. PPARalpha ligands bind and activate the PPARalpha fusion protein and thereby bring about expression of the luciferase reporter gene. The luciferase which is formed can be detected by means of chemiluminescence via an appropriate substrate.

Construction of the Cell Line

The PPARalpha reporter cell line was prepared in 2 stages. Firstly, the luciferase reporter element was constructed and stably transfected into HEK cells. For this purpose, five binding sites of the yeast transcription factor GAL4 (each 5'-CGGAGTACTGTCCTCCGAG-3') (SEQ ID No. 1) were cloned in 5'-upstream of a 68 bp-long minimal MMTV promoter (Genbank Accession # V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete *Photinus pyralis* gene (Genbank Accession # M15077) was cloned in 3'-downstream of the GAL4-

MMTV element. After sequencing, the luceriferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene. In a second step, the PPARalpha fusion protein (GR-GAL4-humanPPARalpha-LBD) was introduced into the stable cell clone described. For this purpose, initially the cDNA coding for the N-terminal 76 amino acids of the glucocorticoid receptor (Genbank Accession # P04150) was linked to the cDNA section coding for amino acids 1-147 of the yeast transcription factor GAL4 (Genbank Accession # P04386). The cDNA of the ligand-binding domain of the human PPARalpha receptor (amino acids S167-Y468; Genbank Accession # S74349) was cloned in at the 3'-end of this GR-GAL4 construct. The fusion construct prepared in this way (GR-GAL4-humanPPARalpha-LBD) was recloned into the plasmid pcDNA3 (from Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay which is described below:

Day 1

The PPARalpha reporter cell line is cultivated to 80% confluence in DMEM (# 41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (# 353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin).

Test substances are tested in 11 different concentrations in the range from 10 µM to 100 pM. More potent compounds are tested in concentration ranges from 1 pM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 µl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

The PPARalpha EC50 values for the compounds of Examples 1 to 62 in this assay are in the range from 0.01 nM to >10 µM.

The results for the activity of some compounds of the invention of the formula I are indicated in Table I below:

TABLE I

| Example No. | EC50 PPARalpha [nM] |
| --- | --- |
| I | 1.9 |
| II | 4.9 |
| VII | 1.7 |
| VIII | 96 |
| IX | 0.13 |
| XII | 0.07 |
| XV | 31 |
| XVI | 38 |
| XVII | 84 |
| XXII | 3.3 |
| XXXIX | 0.17 |
| XLV | 90 |

It is evident from Table I that the compounds of the invention of the formula I activate the PPARalpha receptor and thus bring about for example in analogy to fibrates in clinical use a lowering of triglycerides in the body (see, for example, J.-Ch. Fruchard et al.: PPARS, Metabolic Disease and Atherosclerosis, Pharmacological Research, Vol. 44, No. 5, 345-52, 2001; S. Kersten et al.: Roles of PPARs in health and disease, NATURE, VOL 405, 25 MAY 2000, 421-4; I. Pineda et al.: Peroxisome proliferator-activated receptors: from transcriptional control to clinical practice, Curr Opin Lipidol 12: 2001, 245-254).

Determination of EC50 values of PPAR agonists in the cellular PPARgamma assay

Principle

A transient transfection system is employed to determine the cellular PPARgamma activity of PPAR agonists. It is based on the use of a luciferase reporter plasmid (pGL3basic-5xGAL4-TK) and of a PPARgamma expression plasmid (pcDNA3-GAL4-humanPPARgammaLBD). Both plasmids are transiently transfected into human embryonic kidney cells (HEK cells). There is then expression in these cells of the fusion protein GAL4-humanPPARgammaLBD which binds to the GAL4 binding sites of the reporter plasmid. In the presence of a PPARgamma-active ligand, the activated fusion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARgamma assay the two components (luciferase reporter plasmid and PPARgamma expression plasmid) are transiently transfected into HEK cells because stable and permanent expression of the PPARgamma fusion protein is cytotoxic.

Construction of the Plasmids

The luciferase reporter plasmid pGL3basic-5xGAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3') (SEQ ID No. 2), together with a 160 bp-long thymidine kinase promoter section (Genbank Accession # AF027128) 5'-upstream into pGL3basic. 3'-downstream of the thymidine kinase promoter is the complete luciferase gene from *Photinus pyralis* (Genbank Accession # M15077) which is already a constituent of the plasmid pGL3basic used. The cloning and sequencing of the reporter plasmid pGL3basic-5xGAL4-TK took place in analogy to the description in Sambrook J. et. al. (Molecular cloning, Cold Spring Harbor Laboratory Press, 1989).

The PPARgamma expression plasmid pcDNA3-GAL4-humanPPARgammaLBD was prepared by first cloning the cDNA coding for amino acids 1-147 of the yeast transcription factor GAL4 (Genbank Accession # P04386) into the plasmid pcDNA3 (from Invitrogen) 3'-downstream of the cytomegalovirus promoter. Subsequently, the cDNA of the ligand-binding domain (LBD) of the human PPARgamma receptor (amino acids I152-Y475; Accession # g1480099) 3'-downstream of the GAL4 DNA binding domain. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5xGAL4-TK and the PPARgamma expression plasmid pcDNA3-GAL4-humanPPARgammaLBD, also used for the cellular PPARgamma assay are the reference plasmid pRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

Assay Procedure

The activity of PPARgamma agonists is determined in a 4-day assay which is described below. Before the transfection, HEK cells are cultivated in DMEM (# 41965-039, Invitrogen) which is mixed with the following additions: 10% FCS (#16000-044, Invitrogen), 1% penicillin-streptomycin solution (#15140-122, Invitrogen) and 2 mM L-glutamine (#25030-024, Invitrogen).

Firstly, solution A, a transfection mixture which contains all four plasmids previously described in addition to DMEM, is prepared. The following amounts are used to make up 3 ml of solution A for each 96 well microtiter plate for an assay: 2622 µl of antibiotic- and serum-free DMEM (# 41965-039, Invitrogen), 100 µl of reference plasmid pRL-CMV (1 ng/µl), 100 µl of luciferase reporter plasmid pGL3basic-5xGAL4-TK (10 ng/µl), 100 µl of PPARgamma expression plasmid pcDNA3-GAL4-humanPPARgammaLBD (100 ng/µl) and 78 µl of plasmid pBluescript SK(+) (500 ng/µl). Then 2 ml of solution B are prepared by mixing 1.9 ml of DMEM (# 41965-039, Invitrogen) with 100 µl of PolyFect transfection reagent (from Qiagen) for each 96 well microtiter plate. Subsequently, 3 ml of solution A are mixed with 2 ml of solution B to give 5 ml of solution C, which is thoroughly mixed by multiple pipetting and incubated at room temperature for 10 min. 80%-confluent HEK cells from a cell culture bottle with a capacity of 175 $cm^2$ are washed once with 15 ml of PBS (#14190-094, Invitrogen) and treated with 3 ml of trypsin solution (#25300-054, Invitrogen) at 37° C. for 2 min. The cells are then taken up in 15 ml of DMEM (# 41965-039, Invitrogen) which is mixed with 10% FCS (# 16000-044, Invitrogen), 1% penicillin-streptomycin solution (#15140-122, Invitrogen) and 2 mM L-glutamine (#25030-024, Invitrogen). After the cell suspension has been counted in a cell counter, the suspension is diluted to 250,000 cells/ml. 15 ml of this cell suspension are mixed with 5 ml of solution C for one microtiter plate. 200 µl of the suspension are seeded in each well of a 96 well microtiter plate with a clear plastic base (#3610, Corning Costar). The plates are incubated in a cell culture incubator at 37° C. and 5% $CO_2$ for 24 h.

Day 2

PPAR agonists to be tested are dissolved in DMSO in a concentration of 10 mM. This stock solution is diluted in DMEM (# 41965-039, Invitrogen) which is mixed with 2% Ultroser (#12039-012, Biosepra), 1% penicillin-streptomycin solution (#15140-122, Invitrogen) and 2 mM L-glutamine (#25030-024, Invitrogen). Test substances are tested in a total of 11 different concentrations in the range from 10 µM to 100 pM. More potent compounds are tested in concentration ranges from 1 µM to 10 pM.

The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. Each plate is charged with a standard PPARgamma agonist, which is likewise diluted in 11 different concentrations, in order to demonstrate the functioning of the assay in each individual plate. The assay plates are incubated in an incubator at 37° C. and 5% $CO_2$.

Day 4

After removal of the medium by aspiration, 50 µl of Dual-Glo™ reagent (Dual-Glo™ Luciferase Assay System; Promega) are added to each well in accordance with the manufacturer's instructions in order to lyze the cells and provide the substrate for the firefly luciferase (*Photinus pyralis*) formed in the cells. After incubation at room temperature in the dark for 10 minutes, the firefly luciferase-mediated chemiluminescence is measured in a measuring instrument (measuring time/well 1 sec; Trilux from Wallac). Then 50 µl of the Dual-Glo™ Stop & Glo reagent (Dual-Glo™ Luciferase Assay System; Promega) is added to each well in order to stop the activity of the firefly luciferase and provide the substrate for the Renilla luciferase expressed by the reference plasmid PRL-CMV. After incubation at room temperature in the dark for a further 10 minutes, a chemiluminescence mediated by the Renilla luciferase is again measured for 1 sec/well in the measuring instrument.

Evaluation

The crude data from the luminometer are transferred into a Microsoft Excel file. The firefly/Renilla luciferase activity ratio is determined for each measurement derived from one well of the microtiter plate. The dose-effect plots and EC50 values of PPAR agonists are calculated from the ratios by the XL.Fit program as specified by the manufacturer (IDBS). PPARgamma EC50 values in the range from 50 nM to >10 µM were measured for the PPAR agonists described in this application.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

The examples given in Table II serve to illustrate the invention, but without limiting it.

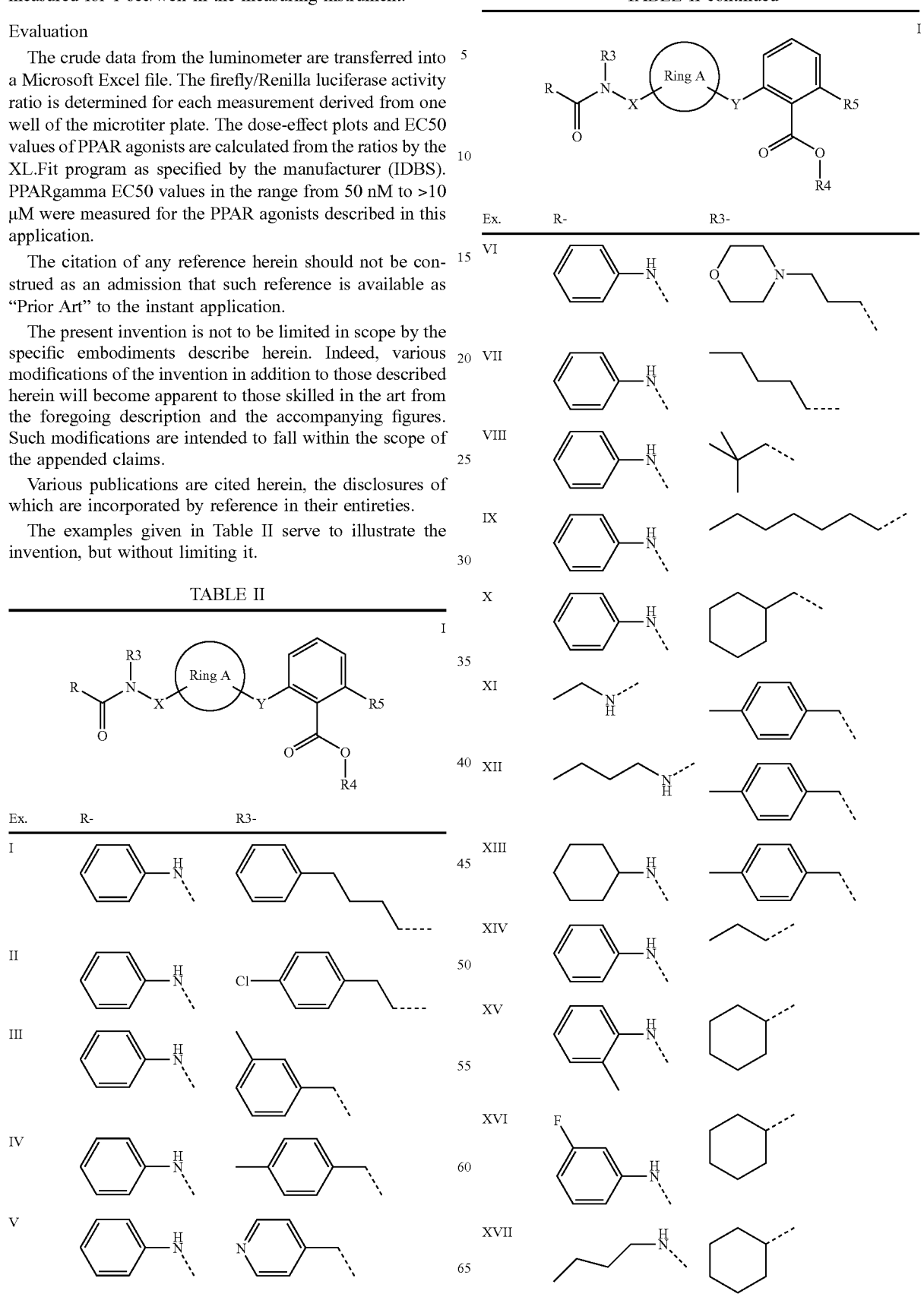

TABLE II-continued

| Ex. | R- | R3- |
|---|---|---|
| XVIII | 2-methylphenyl-NH- | cyclohexylmethyl |
| XIX | 3-fluorophenyl-NH- | cyclohexylmethyl |
| XX | 2-methylphenyl-NH- | 2,4-dimethylpentan-3-yl |
| XXI | 3-fluorophenyl-NH- | 2,4-dimethylpentan-3-yl |
| XXII | n-butyl-NH- | 2,4-dimethylpentan-3-yl |
| XXIII | 2-methylphenyl-NH- | pentan-3-yl |
| XXIV | 3-fluorophenyl-NH- | pentan-3-yl |
| XXV | n-butyl-NH- | pentan-3-yl |
| XXVI | 2-methylphenyl-NH- | butan-2-yl |
| XXVII | 3-fluorophenyl-NH- | butan-2-yl |
| XXVIII | 2-methylphenyl-NH- | 3-methylbenzyl |
| XXIX | 3-fluorophenyl-NH- | 3-methylbenzyl |
| XXX | n-butyl-NH- | 3-methylbenzyl |
| XXXI | 2-methylphenyl-NH- | neopentyl |
| XXXII | n-butyl-NH- | neopentyl |
| XXXIII | 2-methylphenyl-NH- | 3,3-dimethylbutyl |
| XXXIV | 3-fluorophenyl-NH- | 3,3-dimethylbutyl |
| XXXV | 2-methylphenyl-NH- | n-pentyl |
| XXXVI | 2-methylphenyl-NH- | n-heptyl |
| XXXVII | 3-fluorophenyl-NH- | n-heptyl |

TABLE II-continued (Structure I with R-C(O)-N(R3)-X-RingA-Y-C6H3(R5)(C(O)-O-R4))

| Ex. | R- | R3- |
|---|---|---|
| XXXVIII | 4-F-C6H4-NH- | n-octyl |
| XXXIX | n-butyl-NH- | n-octyl |
| XL | 2-methyl-C6H4-NH- | isobutyl (sec-butyl branched) |
| XLI | 3-F-C6H4-NH- | isobutyl |
| XLII | 4-F-C6H4-NH- | isobutyl |
| XLIII | n-butyl-NH- | isobutyl |
| XLIV | 2-methyl-C6H4-NH- | cyclopropyl |
| XLV | 3-F-C6H4-NH- | cyclopropyl |
| XLVI | 4-F-C6H4-NH- | cyclopropyl |
| XLVII | n-butyl-NH- | cyclopropyl |
| XLVIII | 2-methyl-C6H4-NH- | benzyl |
| XLIX | 3-F-C6H4-NH- | benzyl |
| L | 4-F-C6H4-NH- | benzyl |
| LI | n-butyl-NH- | benzyl |
| LII | 2-methyl-C6H4-NH- | pyridin-3-ylmethyl |
| LIII | 3-F-C6H4-NH- | pyridin-3-ylmethyl |
| LIV | 4-F-C6H4-NH- | pyridin-3-ylmethyl |
| LV | n-butyl-NH- | pyridin-3-ylmethyl |
| LVI | 3-F-C6H4-NH- | isobutyl (2-methylbutyl) |
| LVII | sec-butyl | 2-methylbutyl |
| LVIII | 2-methyl-C6H4-NH- | cyclopentyl |

TABLE II-continued

| Ex. | R- | R3- |
|---|---|---|
| LIX | 3-fluorophenyl | cyclopentyl |
| LX | 4-fluorophenyl | cyclopentyl |
| LXI | n-butyl | cyclopentyl |
| LXII | phenyl | 2-chlorophenyl |

In the examples, ring A = cis-cyclohexane-1,3-diyl, R5 = methyl, R4 = H, X = O(CH$_2$)$_2$ and Y = OCH$_2$.
Broken lines indicate the point of attachment of the substituent.

The compounds of the formula I according to the invention can be obtained according to the reaction scheme below:

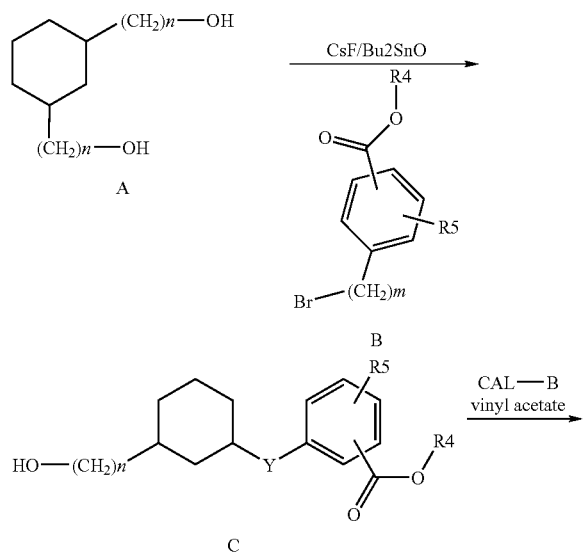

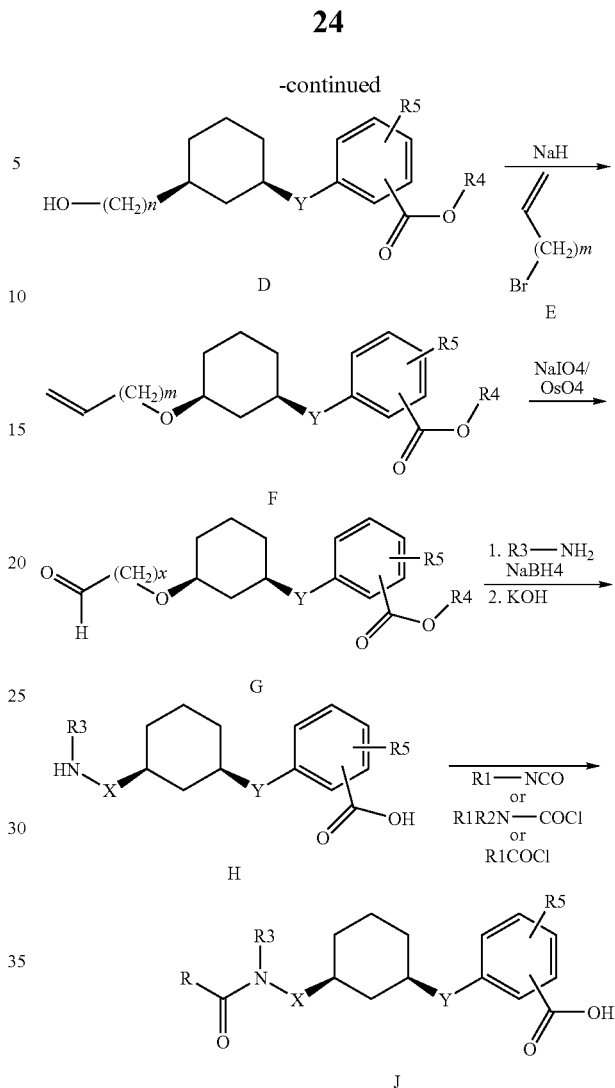

The compound of the general formula A in which n=0-2 is heated with dibutyltin oxide in toluene under reflux on a water separator. After addition of cesium fluoride and dimethylformamide, the mixture is reacted with a compound of the general formula B in which R4 and R5 are as defined above and in which x=1-4 to give a compound of the general formula C in which Y, R4 and R5 are as defined above.

The compound of the general formula C is converted by stirring with *Candida antarctica* lipase B in vinyl acetate at room temperature into the enantiomerically pure product of the general formula D. The corresponding other enantiomer is removed chromatographically by known methods.

The compound of the general formula C or D is deprotonated with sodium hydride in dimethylformamide or tetrahydrofuran and reacted with an alkenyl bromide of the general formula E in which m=0-2 at room temperature to give the racemic (starting from c) or enantiomerically pure (starting from D) compound of the general formula F.

The respective racemic or enantiomerically pure compound of the general formula F is reacted with sodium periodate and osmium tetroxide in diethyl ether at 0° C. to give the racemic or enantiomerically pure aldehyde of the general formula G.

The compound of the general formula G is reacted with primary amines R3-NH$_2$, in which R3 is as defined above, with addition of sodium borohydride in methanol at room temperature. The ester is hydrolyzed by reacting the substance in a tertiary alcohol (for example tert-butanol) with potassium hydroxide to give the racemic or enantiomerically pure compound of the general formula H in which X is as defined above.

The compound of the general formula H is reacted with isocyanates R1-NCO or carbamoyl chlorides R1R2N—COCl or carbonyl chlorides R1-COCl in which R1 and R2 are as defined above, to give racemic or enantiomerically pure urea derivatives or carboxamides of the general formula J in which R, R3, R5, X and Y are as defined above, by stirring both starting materials in an aprotic solvent (for example dimethylformamide) at room temperature in the presence of a base (for example pyridine) for a number of hours.

Further compounds of the formula I can be prepared correspondingly or by known processes.

The experimental procedures for preparing the examples mentioned above are described below:

Examples I-XIV were prepared and tested in enantiomerically pure form.

EXAMPLE I

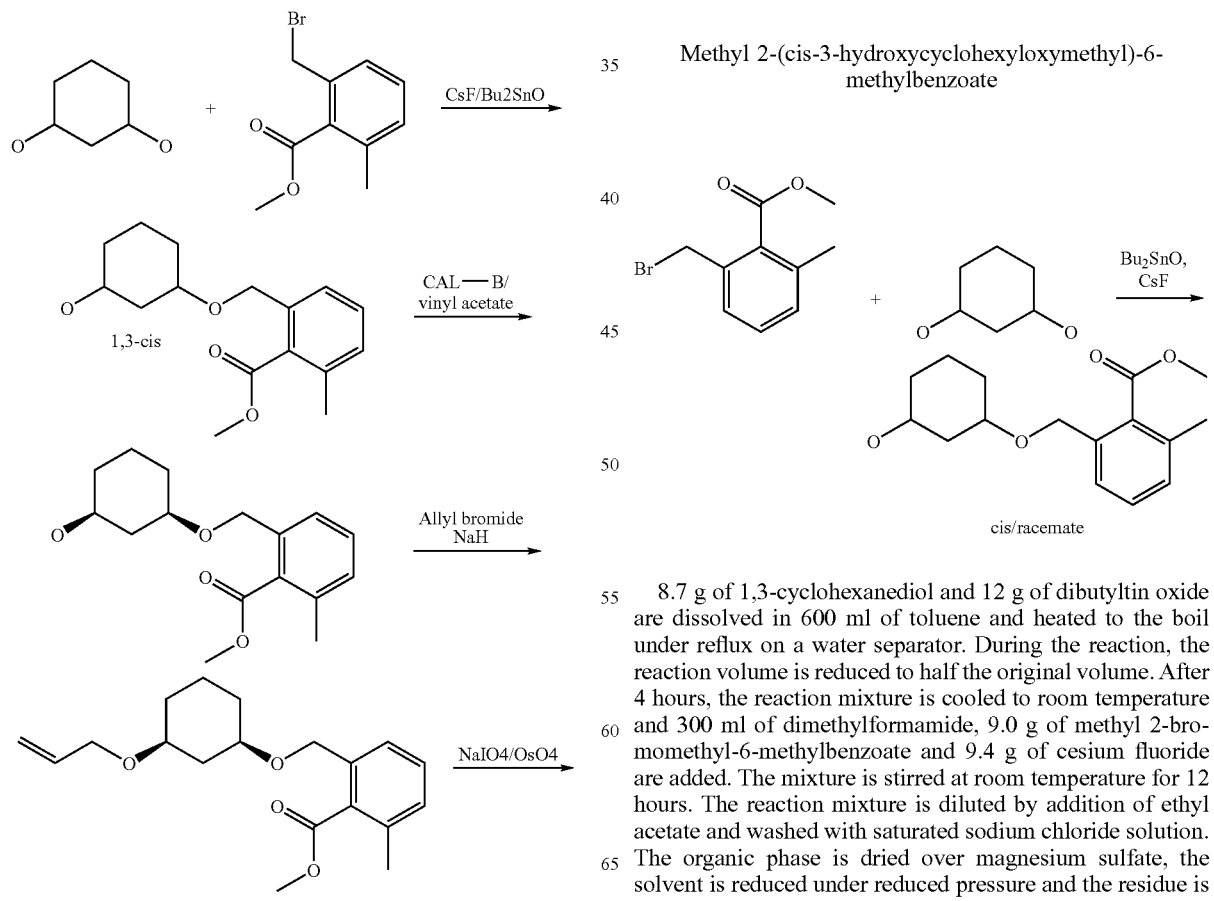

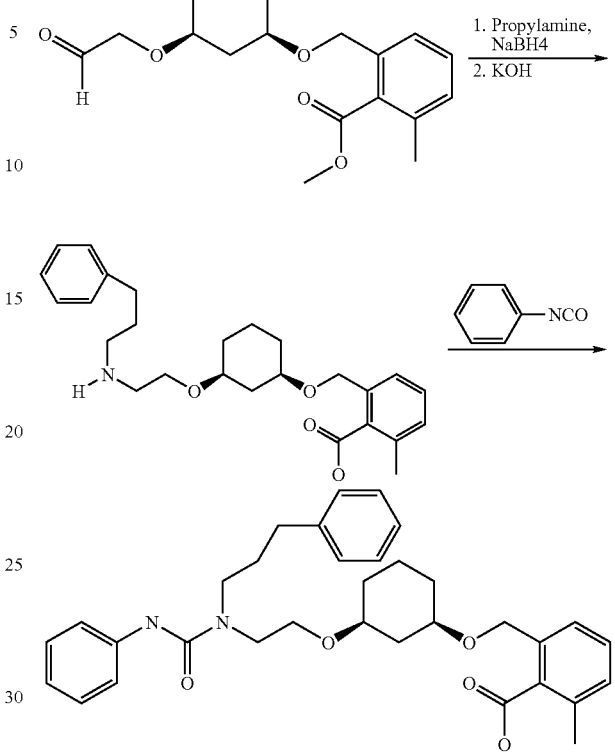

Methyl 2-(cis-3-hydroxycyclohexyloxymethyl)-6-methylbenzoate

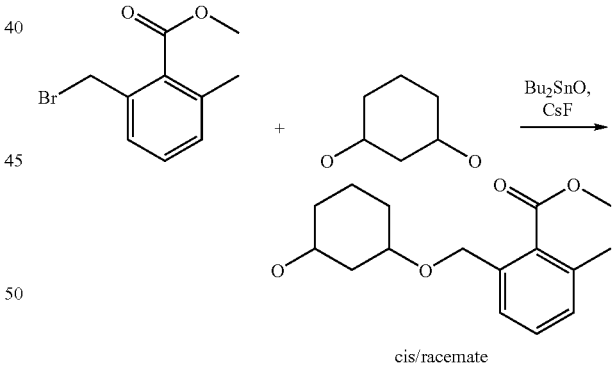

8.7 g of 1,3-cyclohexanediol and 12 g of dibutyltin oxide are dissolved in 600 ml of toluene and heated to the boil under reflux on a water separator. During the reaction, the reaction volume is reduced to half the original volume. After 4 hours, the reaction mixture is cooled to room temperature and 300 ml of dimethylformamide, 9.0 g of methyl 2-bromomethyl-6-methylbenzoate and 9.4 g of cesium fluoride are added. The mixture is stirred at room temperature for 12 hours. The reaction mixture is diluted by addition of ethyl acetate and washed with saturated sodium chloride solution. The organic phase is dried over magnesium sulfate, the solvent is reduced under reduced pressure and the residue is purified by flash chromatography on silica gel (n-heptane/ ethyl acetate=50:1→1:2). This gives 6 g of methyl 2-(cis-3-hydroxycyclohexyloxymethyl)-6-methylbenzoate as an oil. C16H22O4 (278.35), MS(ESI): 279 (M+H+).

Methyl 2-((1R,3S)-3-hydroxycyclohexyloxymethyl)-6-methylbenzoate

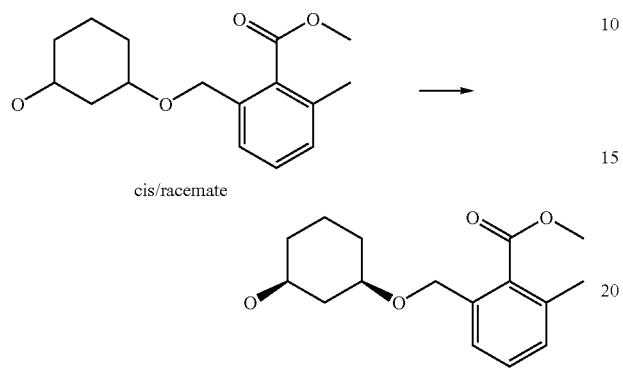

cis/racemate 13.1 g of methyl cis-2-(3-hydroxycyclohexyloxymethyl)-6-methylbenzoate are dissolved in 100 ml of vinyl acetate and 1.6 g of *Candida antartika* lipase B are added. After eight hours of stirring at room temperature, the enzyme is filtered off and the solvent is removed under reduced pressure. The residue is purified by flash chromatography on silica gel (n-heptane/ethyl acetate=10:1→ethyl acetate). This gives 4.3 g of methyl 2-((1R,3S)-3-hydroxycyclohexyloxymethyl)-6-methylbenzoate as a colorless oil. C16H22O4 (278.35), MS(ESI): 279 (M+H+), ee=99% (Chiralpak AD/2 250×4.6; n-heptane:ethanol:methanol=25: 1:0.5+0.1% trifluoroacetic acid, Rt=8.9 min)

Methyl 2-((1R,3S)-3-allyloxycyclohexyloxymethyl)-6-methylbenzoate

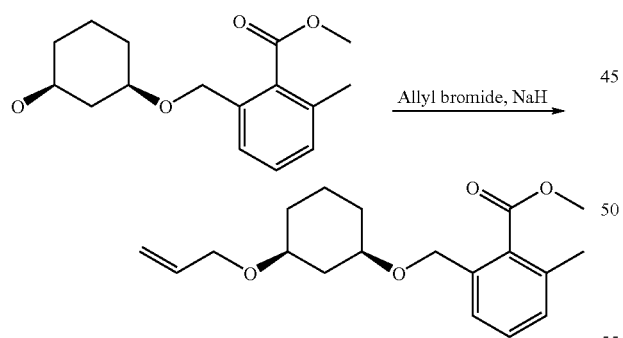

4.3 g of methyl 2-((1R,3S)-3-hydroxycyclohexyloxymethyl)-6-methylbenzoate are dissolved in 40 ml of dimethylformamide and 1.3 g of sodium hydride (60% strength suspension in paraffin oil) are added. After 40 minutes of stirring, 4 ml of allyl bromide, dissolved in 20 ml of tetrahydrofuran, are added. After 3 hours, 300 ml of ethyl acetate are added and the mixture is washed three times with saturated sodium chloride solution. The combined organic phases are dried over sodium sulfate and the solvents are then removed under reduced pressure. The resulting residue is purified on silica gel using the mobile phase n-heptane: ethyl acetate=50:1→5:1. This gives 2.1 g of methyl 2-((1R, 3S)-3-allyloxycyclohexyloxymethyl)-6-methylbenzoate as a yellow oil. C19H26O4 (318.42), MS(ESI): 319 (M+H+).

Methyl 2-methyl-6-[(1R,3S)-3-(2-oxoethoxy)cyclohexyloxymethyl]benzoate

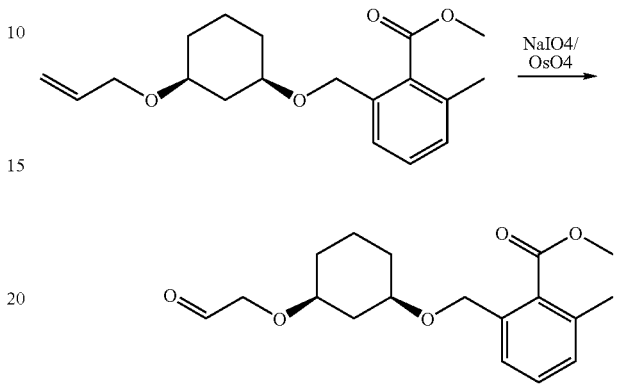

1.0 g of methyl 2-((1R,3S)-3-allyloxycyclohexyloxymethyl)-6-methylbenzoate is dissolved in 30 ml of diethyl ether, and 2.0 g of sodium periodate, dissolved in 30 ml of water, are added. At 0° C., 2 ml of a solution of 2.5% by weight of osmium tetroxide and tert-butanol are added. The reaction mixture is stirred vigorously for three hours. The mixture is then cooled to 0° C., and 50 ml of a saturated sodium thiosulfate solution are added. The organic phase is removed. The aqueous phase is extracted three times with in each case 20 ml of diethyl ether. The combined organic phases are dried over magnesium sulfate and the solvent is then removed under reduced pressure. This gives 1.0 g of methyl 2-methyl-6-[(1R,3S)-3-(2-oxoethoxy)cyclohexyloxymethyl]benzoate as a yellow oil C18H24O5 (320.39), MS(ESI): 321 (M+H+), Rf=0 23 (n-heptane:ethyl acetate=1: 1).

2-Methyl-6-{(1R,3S)-3-[2-(3-phenylpropylamino)ethoxy]cyclohexyloxy-methyl}benzoic acid

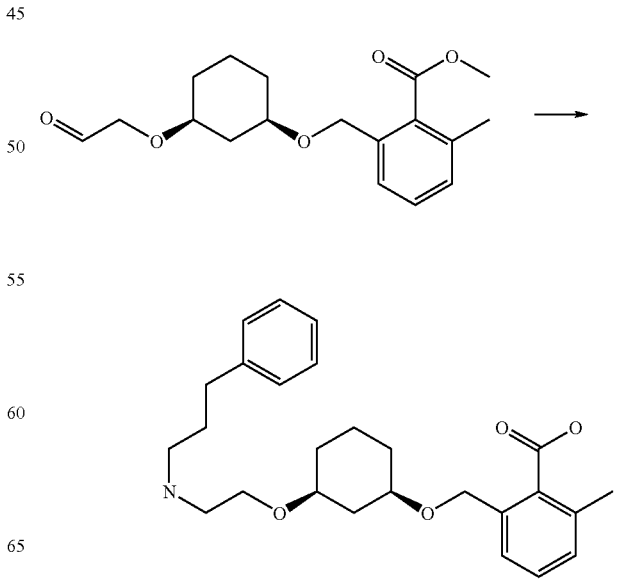

200 mg of methyl 2-methyl-6-[(1R,3S)-3-(2-oxoethoxy) cyclohexyloxy-methyl]benzoate and 90 µl of 3-phenylpropylamine are dissolved in 5 ml of methanol. 300 mg of 4 Å molecular sieve, which had been dried by heating, are added, and the mixture is stirred at room temperature for two hours. 25 mg of sodium borohydride are then added to the reaction mixture. After 30 minutes, 50 ml of ethyl acetate are added and the molecular sieve is removed from the mixture by filtration through celite. The filtrate is concentrated under reduced pressure, the residue is dissolved in 5 ml of tert-butanol and 0.5 ml of 10 N potassium hydroxide solution are added. The mixture is refluxed for 1 day. After addition of 2 ml of water, the organic phase is removed and the aqueous phase is extracted three times with in each case 20 ml of ethyl acetate. The combined organic phases are dried over magnesium sulfate and the solvents are then removed under reduced pressure. This gives 160 mg of 2-methyl-6-{(1R,3S)-3-[2-(3-phenylpropylamino)ethoxy] cyclohexyloxymethyl}benzoic acid as a yellow oil. C26H25NO4 (425.57), MS(ESI): 426 (M+H+).

2-{(1R,3S)-3-[2-(1-[3-Phenylpropyl]-3-phenylureido)ethoxy]cyclohexyl-oxymethyl}-6-methylbenzoic acid

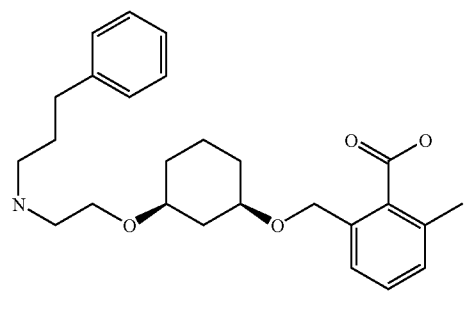

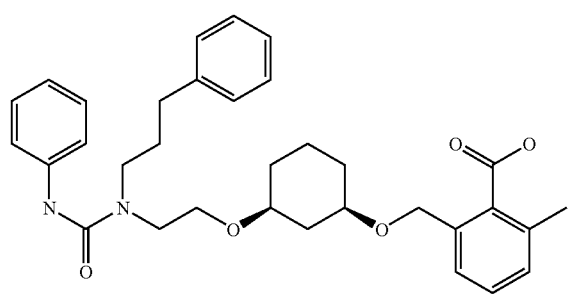

160 mg of 2-methyl-6-{(1R,3S)-3-[2-(3-phenylpropylamino)ethoxy]cyclohexyloxymethyl}benzoic acid are dissolved in 2 ml of dimethylformamide, and 0.1 ml of phenyl isocyanate is added. After 30 minutes, the reaction mixture is purified by RP-HPLC. This gives 54 mg of 2-{(1R,3S)-3-[2-(1-[3-phenylpropyl]-3-phenylureido)ethoxy]cyclo-hexyloxymethyl}-6-methylbenzoic acid as a white lyophilizate. C33H40N2O5 (544.70), MS(ESI): 545 (M+H+).

EXAMPLE II

Analogously to Example I, methyl 2-methyl-6-[(1R,3S)-3-(2-oxoethoxy)cyclohexyloxymethyl]benzoate, 2-(4-chlorophenyl)ethylamine and phenyl isocyanate gave 2-{(1R,3S)-3-[2-(1-[2-(4-chlorophenyl)ethyl]-3-phenylureido)ethoxy]cyclohexyloxymethyl}-6-methylbenzoic acid.

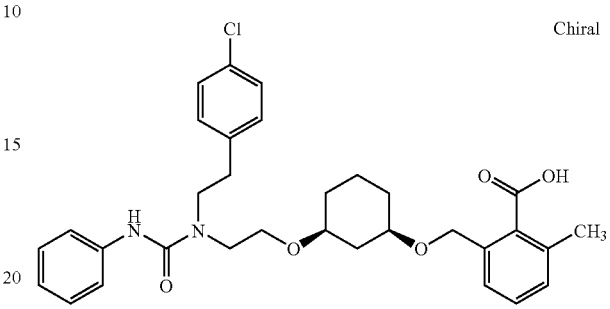

C32H37ClN2O5 (565.11), MS(ESI): 565 (M+H+).

EXAMPLE III

Analogously to Example I, methyl 2-methyl-6-[(1R,3S)-3-(2-oxoethoxy)cyclohexyloxymethyl]benzoate, 3-methylbenzylamine and phenyl isocyanate gave 2-{(1R,3S)-3-[2-(1-(3-methylbenzyl)-3-phenyl-ureido)ethoxy] cyclohexyloxymethyl}-6-methylbenzoic acid.

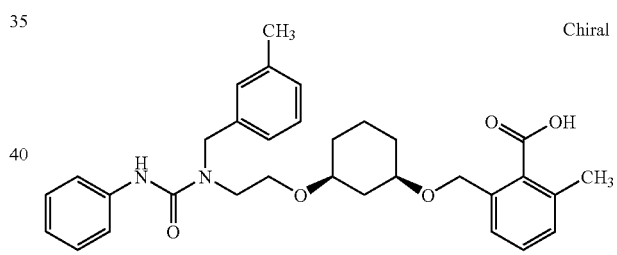

C32H38N2O5 (530.66), MS(ESI): 531.

EXAMPLE IV

Analogously to Example I, methyl 2-methyl-6-[(1R,3S)-3-(2-oxoethoxy)cyclohexyloxymethyl]benzoate, 4-methylbenzylamine and phenyl isocyanate gave 2-{(1R,3S)-3-[2-(1-(4-methylbenzyl)-3-phenylureido)ethoxy] cyclohexyloxymethyl}-6-methylbenzoic acid.

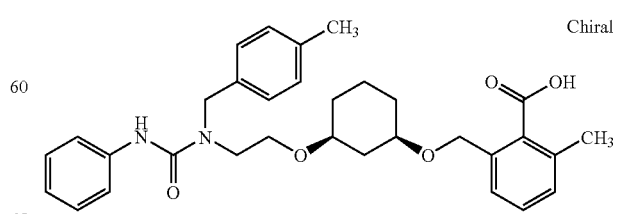

C32 H38 N2 O5 (530.66), MS(ESI): 531.

EXAMPLE V

Analogously to Example I, methyl 2-methyl-6-[(1R,3S)-3-(2-oxoethoxy)cyclohexyloxymethyl]benzoate, pyridin-4-ylmethylamine and phenyl isocyanate gave 2-{(1R,3S)-3-[2-(1-pyridin-4-ylmethyl-3-phenylureido)ethoxy]cyclohexyloxymethyl}-6-methylbenzoic acid.

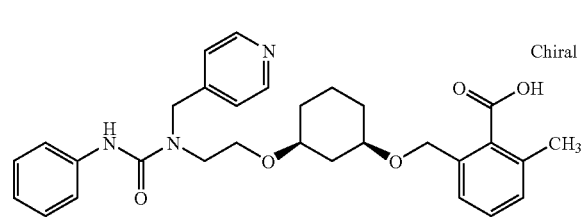

C30 H35 N3 O5 (517.62), MS(ESI): 518.

EXAMPLE VI

Analogously to Example I, methyl 2-methyl-6-[(1R,3S)-3-(2-oxoethoxy)cyclohexyloxymethyl]benzoate, 3-morpholin4-ylpropylamine and phenyl isocyanate gave 2-{(1R,3S)-3-[2-(1-(3-morpholin-4-ylpropyl)-3-phenylureido)ethoxy]cyclohexyloxymethyl}-6-methylbenzoic acid.

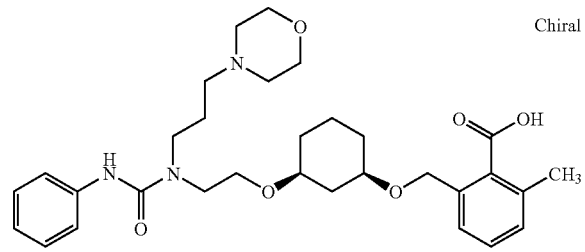

C31 H43 N3 O6 (553.70), MS(ESI): 554.

EXAMPLE VII

Analogously to Example I, methyl 2-methyl-6-[(1R,3S)-3-(2-oxoethoxy)cyclohexyloxymethyl]benzoate, pentylamine and phenyl isocyanate gave 2-{(1 R,3S)-3-[2-(1-pentyl-3-phenylureido)ethoxy]cyclohexyloxymethyl}-6-methylbenzoic acid.

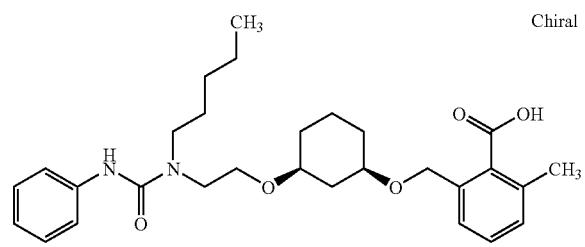

C29 H40 N2 O5 (496.64), MS(ESI): 497.

EXAMPLE VIII

Analogously to Example I, methyl 2-methyl-6-[(1R,3S)-3-(2-oxoethoxy)cyclohexyloxymethyl]benzoate, 2,2-dimethylpropylamine and phenyl isocyanate gave 2-((1R,3S)-3-{2-[1-(2,2-dimethylpropyl)-3-phenylureido]ethoxy}cyclohexyloxymethyl)-6-methylbenzoic acid.

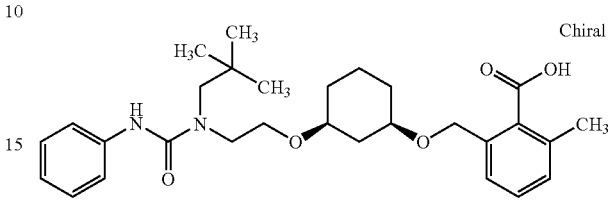

C29H40N2O5 (496.65), MS(ESI): 497.

EXAMPLE IX

Analogously to Example I, methyl 2-methyl-6-[(1R,3S)-3-(2-oxoethoxy)cyclohexyloxymethyl]benzoate, heptylamine and phenyl isocyanate gave 2-{(1R,3S)-3-[2-(1-heptyl-3-phenylureido)ethoxy]cyclohexyloxymethyl}-6-methylbenzoic acid.

A002609939

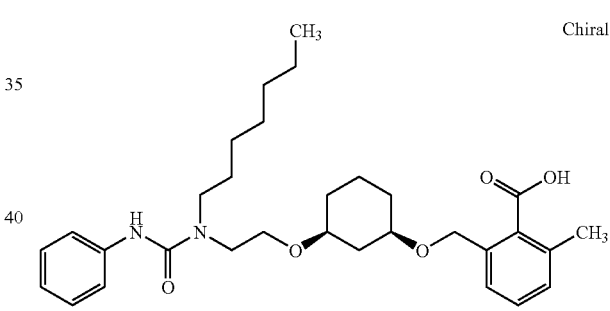

C31H44N2O5 (524.71), MS(ESI): 525.

EXAMPLE X

Analogously to Example I, methyl 2-methyl-6-[(1R,3S)-3-(2-oxoethoxy)cyclohexyloxymethyl]benzoate, cyclohexylmethylamine and phenyl isocyanate gave 2-{(1R,3S)-3-[2-(1-cyclohexylmethyl-3-phenylureido)ethoxy]cyclohexyloxymethyl}-6-methylbenzoic acid.

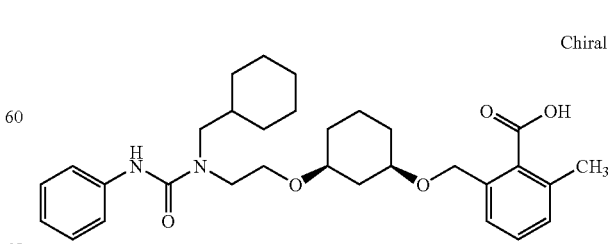

C31H42N2O5 (522.69), MS(ESI): 523.

EXAMPLE XI

Analogously to Example I, methyl 2-methyl-6-[(1R,3S)-3-(2-oxoethoxy)cyclohexyloxymethyl]benzoate, 4-methylbenzylamine and ethyl isocyanate gave 2-((1R,3S)-3-{2-[3-ethyl-1-(4-methylbenzyl)ureido]ethoxy}-cyclohexyloxymethyl)-6-methyl benzoic acid.

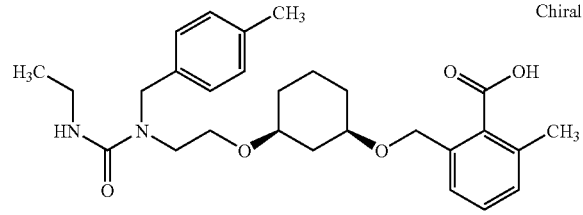

C28H38N2O5 (482.63), MS(ESI): 483.

EXAMPLE XII

Analogously to Example I, methyl 2-methyl-6-[(1R,3S)-3-(2-oxoethoxy)cyclohexyloxymethyl]benzoate, 4-methylbenzylamine and butyl isocyanate gave 2-((1R,3S)-3-{2-[3-butyl-1-(4-methylbenzyl)ureido]ethoxy}-cyclohexyloxymethyl)-6-methylbenzoic acid.

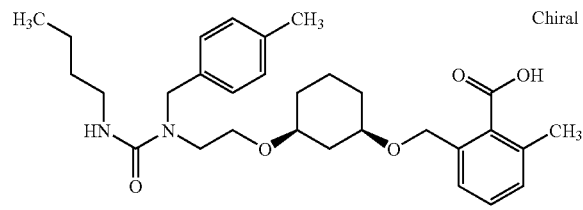

C30H42N2O5 (510.68), MS(ESI): 511.

EXAMPLE XIII

Analogously to Example I, methyl 2-methyl-6-[(1R,3S)-3-(2-oxoethoxy)cyclohexyloxymethyl]benzoate, 4-methylbenzylamine and cyclohexyl isocyanate gave 2-((1R,3S)-3-{2-[3-cyclohexyl-1-(4-methylbenzyl)ureido]ethoxy}cyclohexyloxymethyl)-6-methylbenzoic acid.

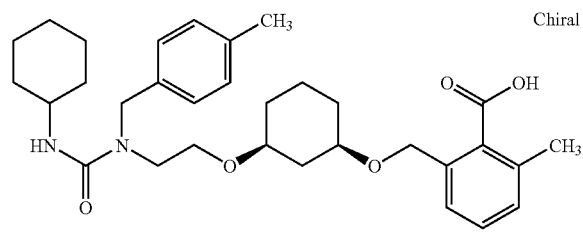

C32H44N2O5 (536.72), MS(ESI): 537.

EXAMPLE XIV

Analogously to Example I, methyl 2-methyl-6-[(1R,3S)-3-(2-oxoethoxy)cyclohexyloxymethyl]benzoate, propylamine and phenyl isocyanate gave 2-methyl-6-{(1R,3S)-3-[2-(3-phenyl-1-propylureido)-ethoxy]cyclohexyloxymethyl}benzoic acid.

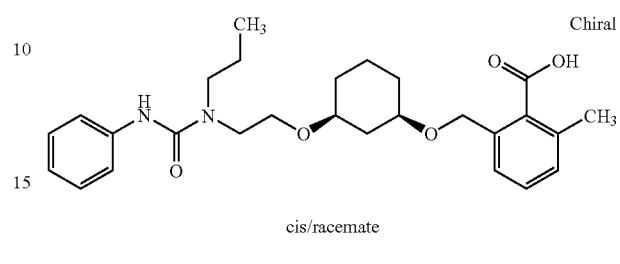

C27H36N2O5 (468.60), MS(ESI): 469.

Examples XV-LXII were prepared and tested as racemic compounds having cis configuration of the two substituents on the cyclohexane ring.

EXAMPLE XV

Analogously to Example I, racemic methyl 2-methyl-6-[cis-3-(2-oxoethoxy)cyclohexyloxymethyl]benzoate, cyclohexylamine and 2-methylphenyl isocyanate gave 2-{cis-3-[2-(1-cyclohexyl-3-o-tolylureido)ethoxy]cyclohexyloxymethyl}-6-methylbenzoic acid.

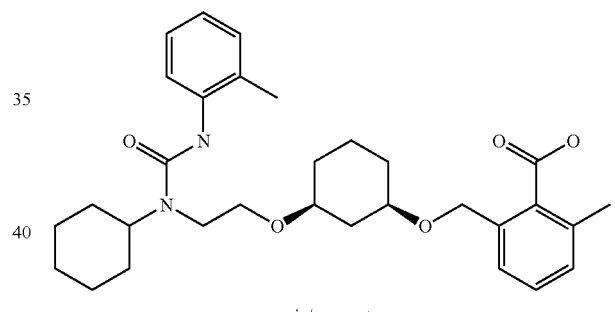

C31H42N2O5 (522.69), MS(ESI): 523 (M+H+).

EXAMPLE XVI

Analogously to Example I, racemic methyl 2-methyl-6-[cis-3-(2-oxoethoxy)cyclohexyloxymethyl]benzoate, cyclohexylamine and 3-fluorophenylisocyanate gave 2-(cis-3-{2-[1-cyclohexyl-3-(3-fluorophenyl)-ureido]ethoxy}cyclohexyloxymethyl)-6-methylbenzoic acid.

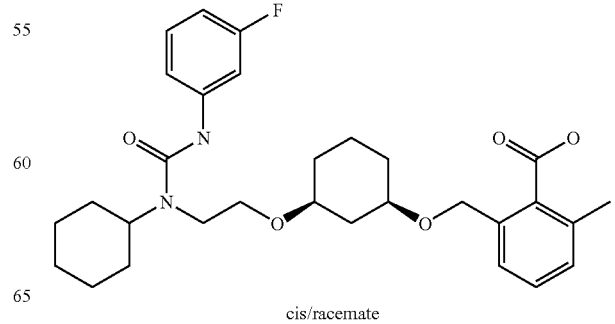

C30H39FN2O5 (526.65), MS(ESI): 527 (M+H+).

EXAMPLE XVII

Analogously to Example I, racemic methyl 2-methyl-6-[cis-3-(2-oxoethoxy)cyclohexyloxymethyl]benzoate, cyclohexylamine and butyl isocyanate gave 2-{cis-3-[2-(3-butyl-1-cyclohexylureido)ethoxy]cyclohexyloxymethyl}-6-methylbenzoic acid.

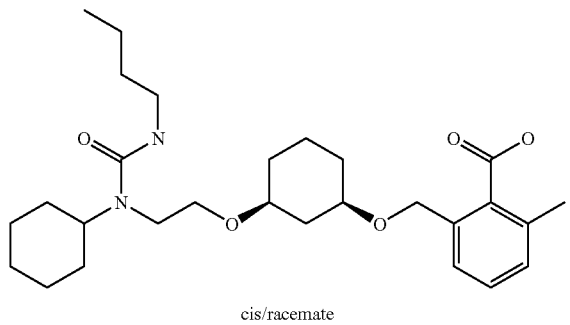

cis/racemate

C28H44N2O5 (488.67), MS(ESI): 489 (M+H+).

EXAMPLE XVIII

Analogously to Example I, racemic methyl 2-methyl-6-[cis-(2-oxoethoxy)cyclohexyloxymethyl]benzoate, cyclohexylmethylamine and 2-methyl phenyl isocyanate gave 2-{cis-3-[2-(1-cyclohexylmethyl-3-o-tolylureido)ethoxy]cyclohexyloxymethyl}-6-methylbenzoic acid.

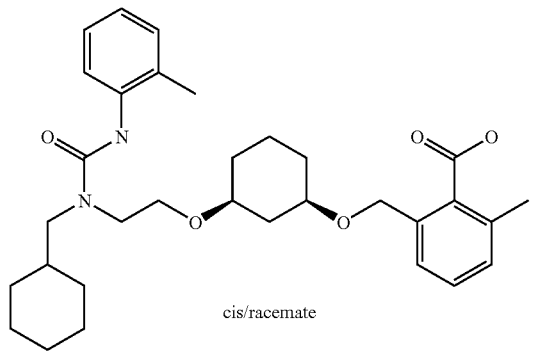

cis/racemate

C32H44N2O5 (536.72), MS(ESI): 537 (M+H+).

EXAMPLE XIX

Analogously to Example I, racemic methyl 2-methyl-6-[cis-3-(2-oxoethoxy)cyclohexyloxymethyl]benzoate, cyclohexylmethylamine and 3-fluorophenylisocyanate gave 2-(cis-3-{2-[1-cyclohexylmethyl-3-(3-fluorophenyl)ureido]ethoxy}cyclohexyloxymethyl)-6-methylbenzoic acid.

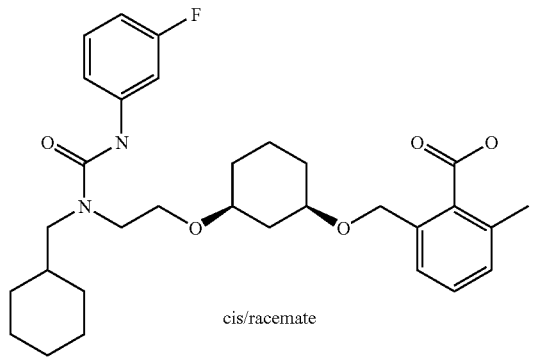

cis/racemate

C31H41FN2O5 (540.68), MS(ESI): 541 (M+H+).

EXAMPLE XX

Analogously to Example I, racemic methyl 2-methyl-6-[cis-3-(2-oxoethoxy)cyclohexyloxymethyl]benzoate, 1,3-dimethylbutylamine and 2-methyl phenyl isocyanate gave 2-(cis-3-{2-[1-((1R)/(1S),3-dimethylbutyl)-3-o-tolylureido]ethoxy}cyclohexyloxymethyl)-6-methylbenzoic acid.

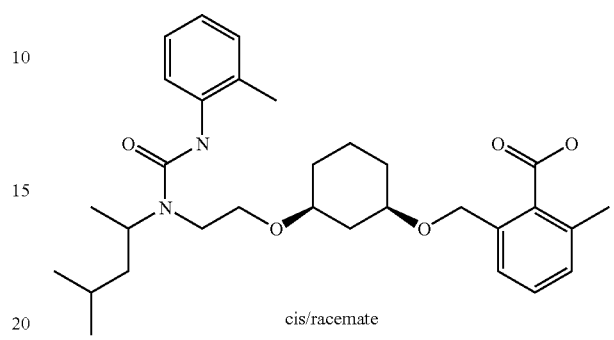

cis/racemate

C31H44N2O5 (524.71), MS(ESI): 525 (M+H+).

EXAMPLE XXI

Analogously to Example I, racemic methyl 2-methyl-6-[cis-3-(2-oxoethoxy)cyclohexyloxymethyl]benzoate, 1,3-dimethylbutylamine and 3-fluorophenyl isocyanate gave (cis-3-{2-[1-((1S)/(1R),3-dimethylbutyl)-3-(3-fluorophenyl)ureido]ethoxy}cyclohexyloxymethyl)-6-methylbenzoic acid.

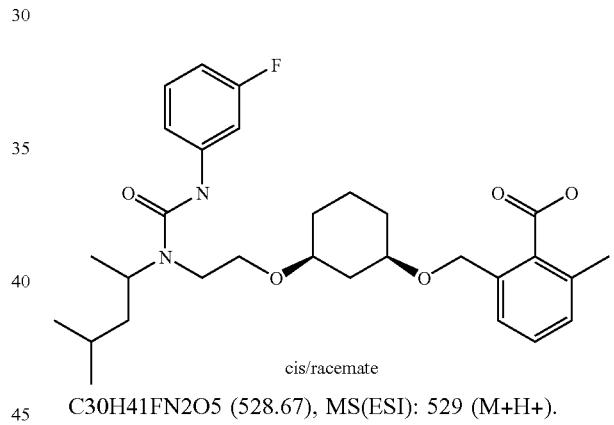

cis/racemate

C30H41FN2O5 (528.67), MS(ESI): 529 (M+H+).

EXAMPLE XXII

Analogously to Example I, racemic methyl 2-methyl-6-[cis-3-(2-oxoethoxy)cyclohexyloxymethyl]benzoate, 1,3-dimethyl butylamine and butyl isocyanate gave 2-(cis-3-{2-[3-butyl-1-((1S)/(1R),3-dimethylbutyl)-ureido]ethoxy}cyclohexyloxymethyl)-6-methylbenzoic acid.

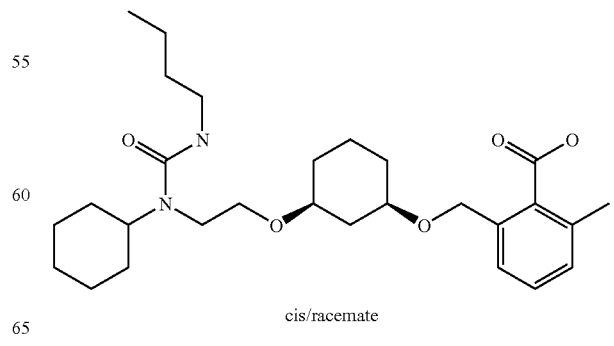

cis/racemate

C28H46N2O5 (490.69), MS(ESI): 491 (M+H+).

EXAMPLE XXIII

Analogously to Example I, racemic methyl 2-methyl-6-[cis-3-(2-oxoethoxy)cyclohexyloxymethyl]benzoate, 1-ethylpropylamine and 2-methylphenyl isocyanate gave 2-(cis-3-{2-[1-(1-ethylpropyl)-3-o-tolylureido]ethoxy}cyclohexyloxymethyl)-6-methylbenzoic acid.

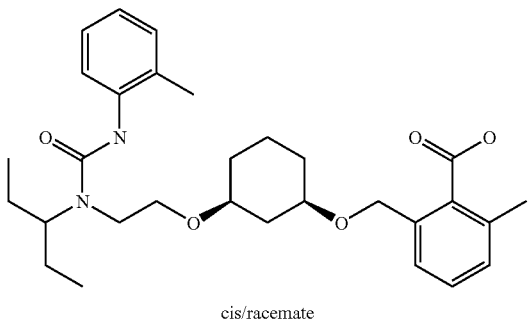

cis/racemate

C30H42N2O5 (510.68) MS(ESI): 511.

EXAMPLE XXIV

Analogously to Example I, racemic methyl 2-methyl-6-[cis-3-(2-oxoethoxy)cyclohexyloxymethyl]benzoate, 1-ethylpropylamine and 3-fluorophenyl isocyanate gave 2-(cis-3-{2-[1-(1-ethylpropyl)-3-(3-fluorophenyl)ureido]ethoxy}cyclohexyloxymethyl)-6-methylbenzoic acid.

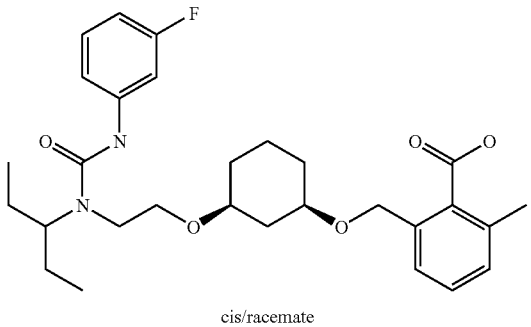

cis/racemate

C29H39FN2O5 (514.64), MS(ESI): 515 (M+H+).

EXAMPLE XXV

Analogously to Example I, racemic methyl 2-methyl-6-[cis-3-(2-oxoethoxy)cyclohexyloxymethyl]benzoate, 1-ethylpropylamine and butyl isocyanate gave 2-(cis-3-{2-[3-butyl-1-(1-ethylpropyl)ureido]ethoxy}cyclohexyloxymethyl)-6-methylbenzoic acid.

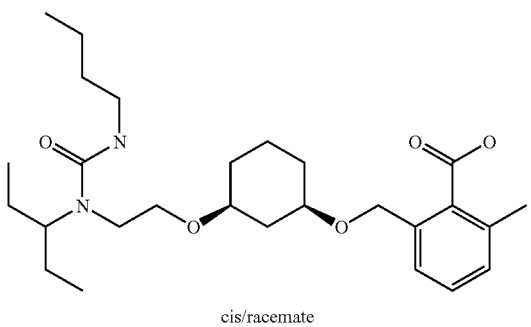

cis/racemate

C27H44N2O5 (476.66), MS(ESI): 477 (M+H+).

EXAMPLE XXVI

Analogously to Example I, racemic methyl 2-methyl-6-[cis-3-(2-oxoethoxy)cyclohexyloxymethyl]benzoate, 1-methylbutylamine and 2-methylphenyl isocyanate gave 2-methyl-6-(cis-3-{2-[1(-methylbutyl)-3-o-tolylureido]ethoxy}cyclohexyloxymethyl)benzoic acid.

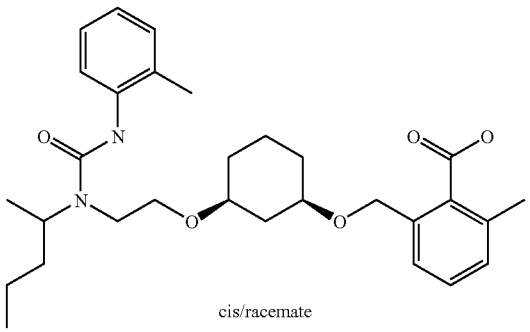

cis/racemate

C30H42N2O5 (510.68), MS(ESI): 511 (M+H+).

EXAMPLE XXVII

Analogously to Example I, racemic methyl 2-methyl-6-[cis-3-(2-oxoethoxy)cyclohexyloxymethyl]benzoate, 1-methylbutylamine and 3-fluorophenylisocyanate gave 2-(cis-3-{2-[3-(3-fluorophenyl)-1-(methylbutyl)ureido]ethoxy}cyclohexyloxymethyl)-6-methylbenzoic acid.

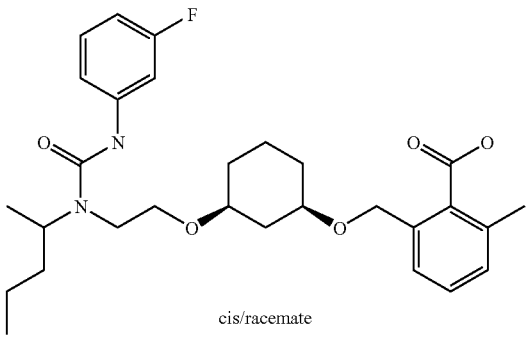

cis/racemate

C29H39FN2O5 (514.64), MS(ESI): 515 (M+H+).

EXAMPLE XXVIII

Analogously to Example I, racemic methyl 2-methyl-6-[cis-3-(2-oxoethoxy)cyclohexyloxymethyl]benzoate, 3-methylbenzylamine and 2-methylphenyl isocyanate gave 2-methyl-6-(cis-3-{2-[1-(3-methylbenzyl)-3-o-tolylureido]ethoxy}cyclohexyloxymethyl)benzoic acid.

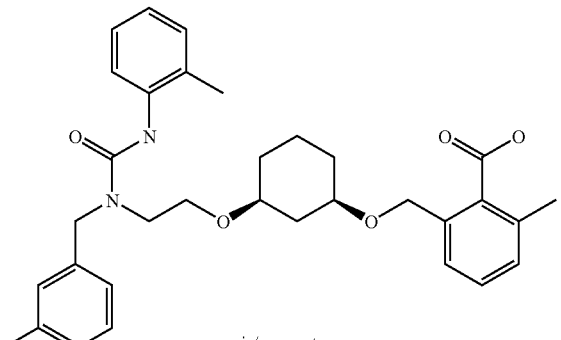

cis/racemate

C33H40N2O5 (544.70), MS(ESI): 545 (M+H+). 544.2937

EXAMPLE XXIX

Analogously to Example I, racemic methyl 2-methyl-6-[cis-3-(2-oxoethoxy)cyclohexyloxymethyl]benzoate, 3-methylbenzylamine and 3-fluorophenyl isocyanate gave 2-(cis-3-{2-[3-(3-fluorophenyl)-1-(3-methylbenzyl)ureido]ethoxy}cyclohexyloxymethyl)-6-methylbenzoic acid.

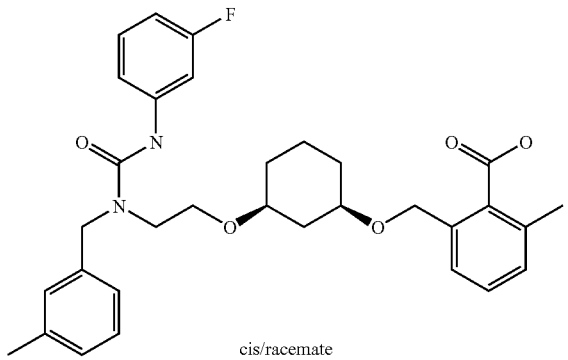

cis/racemate

C32H37FN2O5 (548.66), MS(ESI): 549 (M+H+). 548.2687

EXAMPLE XXX

Analogously to Example I, racemic methyl 2-methyl-6-[cis-3-(2-oxoethoxy)cyclohexyloxymethyl]benzoate, 3-methylbenzylamine and butyl isocyanate gave 2-(cis-3-{2-[3-butyl-1-(3-methylbenzyl)ureido]ethoxy}cyclohexyloxymethyl)-6-methylbenzoic acid.

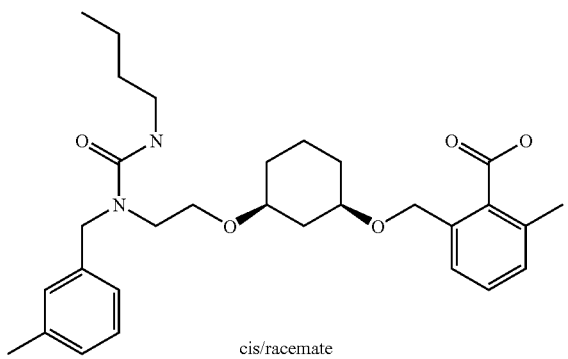

cis/racemate

C30H42N2O5 (510.68), MS(ESI): 511 (M+H+).

EXAMPLE XXXI

Analogously to Example I, racemic methyl 2-methyl-6-[cis-3-(2-oxoethoxy)cyclohexyloxymethyl]benzoate, 2,2-dimethylpropylamine and 2-methylphenylisocyanate gave 2-(cis-3-{2-[1-(2,2-d imethylpropyl )-3-o-tolylureido]ethoxy}cyclohexyloxymethyl)-6-methylbenzoic acid.

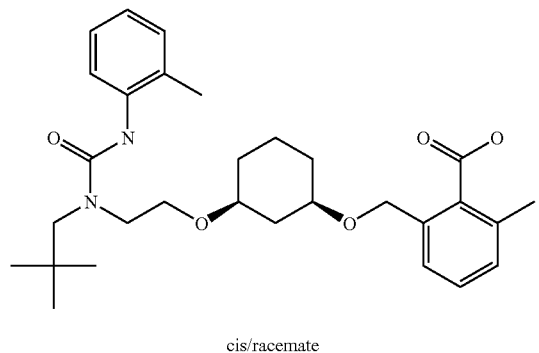

cis/racemate

C30H42N2O5 (510.68), MS(ESI): 511 (M+H+).

EXAMPLE XXXII

Analogously to Example I, racemic methyl 2-methyl-6-[cis-3-(2-oxoethoxy)cyclohexyloxymethyl]benzoate, 2,2-dimethylpropylamine and butyl isocyanate gave 2-(cis-3-{2-[3-butyl-1-(2,2-dimethylpropyl)ureido]-ethoxy}cyclohexyloxymethyl)-6-methylbenzoic acid.

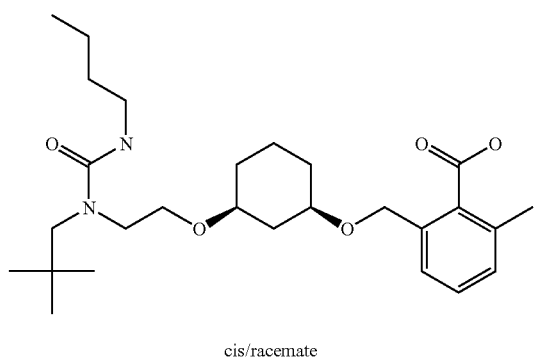

cis/racemate

C27H44N2O5 (476.66), MS(ESI): 477 (M+H+).

EXAMPLE XXXIII

Analogously to Example I, racemic methyl 2-methyl-6-[cis-3-(2-oxoethoxy)cyclohexyloxymethyl]benzoate, 3,3-dimethylbutylamine and 2-methylphenylisocyanate gave 2-(cis-3-{2-[1-(3,3-dimethylbutyl)-3-o-tolylureido]ethoxy}cyclohexyloxymethyl)-6-methylbenzoic acid.

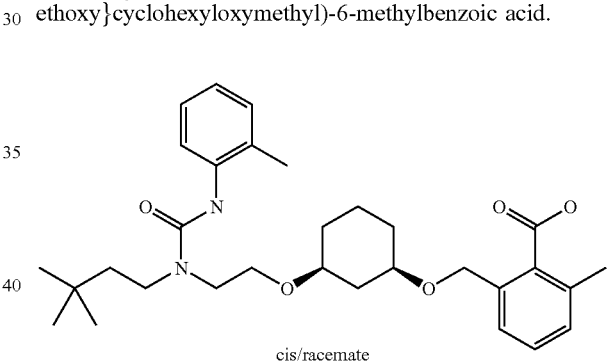

cis/racemate

C31H44N2O5 (524.71), MS(ESI): 525 (M+H+).

EXAMPLE XXXIV

Analogously to Example I, racemic methyl 2-methyl-6-[cis-3-(2-oxoethoxy)cyclohexyloxymethyl]benzoate, 3,3-dimethylbutylamine and 3-fluorophenylisocyanate gave 2-(cis-3-{2-[1-(3,3-dimethylbutyl)-3-(3-fluorophenyl)ureido]ethoxy}cyclohexyloxymethyl)-6-methylbenzoic acid.

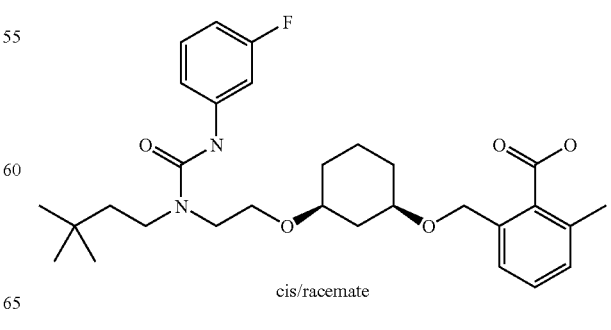

cis/racemate

C30H41FN2O5 (528.67), MS(ESI): 529 (M+H+).

EXAMPLE XXXV

Analogously to Example I, racemic methyl 2-methyl-6-[cis-3-(2-oxoethoxy)cyclohexyloxymethyl]benzoate, pentylamine and 2-methylphenyl isocyanate gave 2-methyl-6-{cis-3-[2-(1-pentyl-3-o-tolylureido)ethoxy]cyclohexyloxymethyl}benzoic acid.

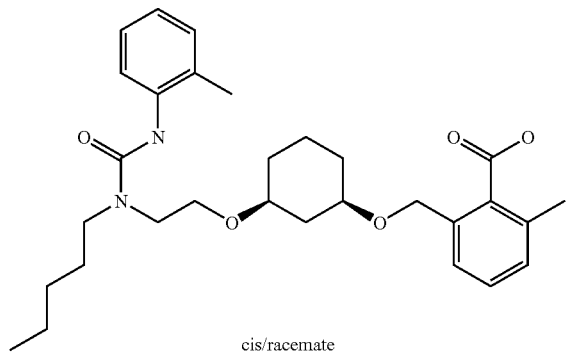

C30H42N2O5 (510.68), MS(ESI): 511 (M+H+).

EXAMPLE XXXVI

Analogously to Example I, racemic methyl 2-methyl-6-[cis-3-(2-oxoethoxy)cyclohexyloxymethyl]benzoate, heptylamine and 2-methylphenyl isocyanate gave 2-{cis-3-[2-(1-heptyl-3-o-tolylureido)ethoxy]cyclohexyloxy-methyl}-6-methylbenzoic acid.

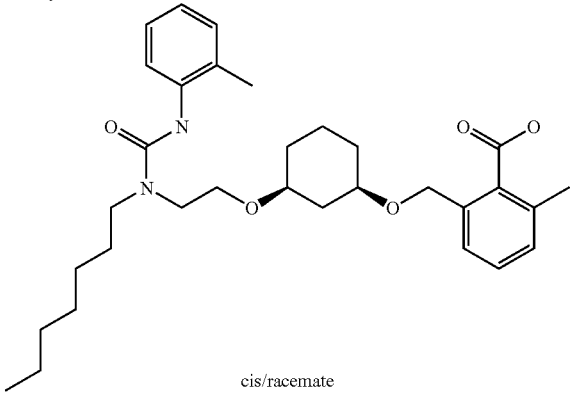

C32H46N2O5 (538.73), MS(ESI): 539 (M+H+).

EXAMPLE XXXVII

Analogously to Example I, racemic methyl 2-methyl-6-[cis-3-(2-oxoethoxy)cyclohexyloxymethyl]benzoate, heptylamine and 3-fluorophenyl isocyanate gave 2-(cis-3-{2-[3-(3-fluorophenyl)-1-heptylureido]ethoxy}cyclohexyloxymethyl)-6-methylbenzoic acid.

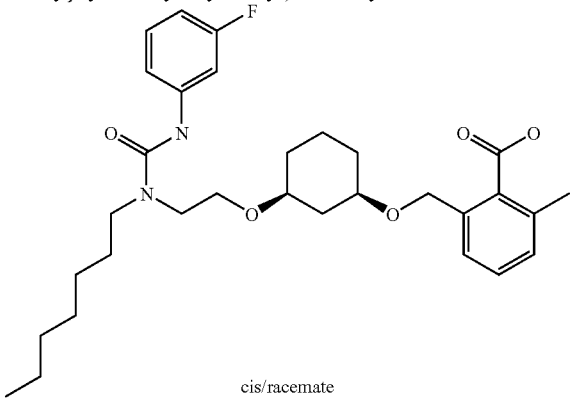

C31H43FN2O5 (542.70), MS(ESI): 543 (M+H+).

EXAMPLE XXXVIII

Analogously to Example I, racemic methyl 2-methyl-6-[cis-3-(2-oxoethoxy)cyclohexyloxymethyl]benzoate, heptylamine and 4-fluorophenyl isocyanate gave 2-(cis-3-{2-[3-(4-fluorophenyl)-1-heptylureido]ethoxy}cyclohexyloxymethyl)-6-methylbenzoic acid.

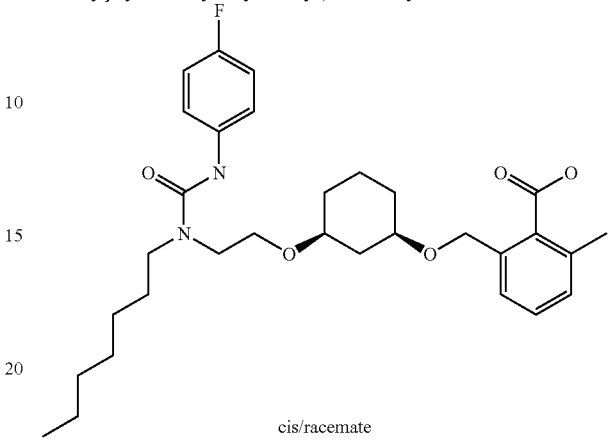

C31H43FN2O5 (542.70), MS(ESI): 542 (M+H+).

EXAMPLE XXXIX

Analogously to Example I, racemic methyl 2-methyl-6-[cis-3-(2-oxoethoxy)cyclohexyloxymethyl]benzoate, heptylamine and butyl isocyanate gave 2-{cis-3-[2-(3-butyl-1-heptylureido)ethoxy]cyclohexyloxy-methyl}-6-methylbenzoic acid.

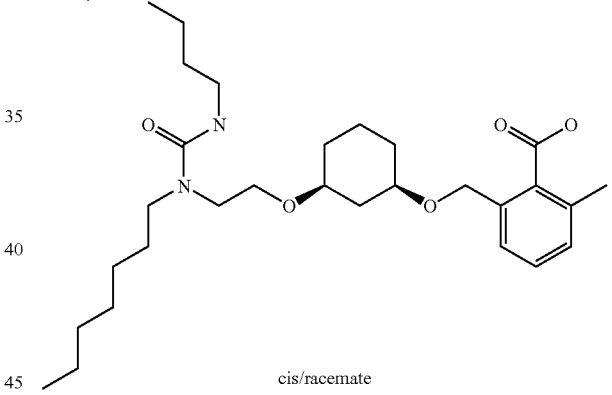

C29H48N2O5 (504.72), MS(ESI): 505 (M+H+).

EXAMPLE XL

Analogously to Example I, racemic methyl 2-methyl-6-[cis-3-(2-oxoethoxy)cyclohexyloxymethyl]benzoate, 1,2-dimethylpropylamine and 2-methylphenylisocyanate gave 2-(cis-3-{2-[1-((1R)/(1S),2-dimethylpropyl)-3-o-tolylureido]ethoxy}cyclohexyloxymethyl)-6-methylbenzoic acid.

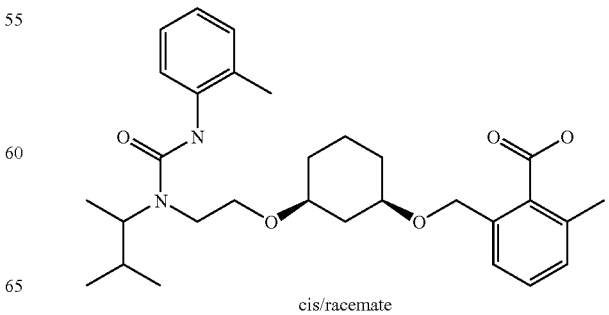

C30H42N2O5 (510.68), MS(ESI): 567 (M+H+).

EXAMPLE XLI

Analogously to Example I, racemic methyl 2-methyl-6-[cis-3-(2-oxoethoxy)cyclohexyloxymethyl]benzoate, 1,2-dimethylpropylamine and 3-fluorophenylisocyanate gave 2-(cis-3-{2-[1-(2-dimethylpropyl)-3-(3-fluorophenyl)ureido]ethoxy}cyclohexyloxymethyl)-6-methylbenzoic acid.

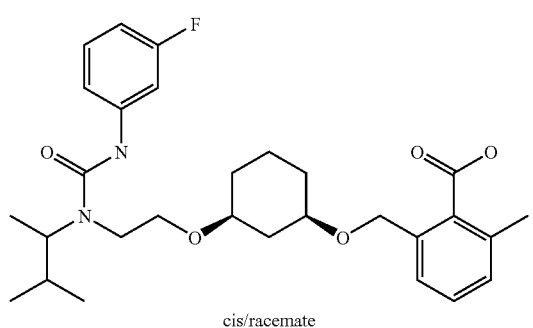

cis/racemate

C29H39FN2O5 (514.64), MS(ESI): 515 (M+H+).

EXAMPLE XLII

Analogously to Example I, racemic methyl 2-methyl-6-[cis-3-(2-oxoethoxy)cyclohexyloxymethyl]benzoate, 1,2-dimethylpropylamine and 4-fluorophenylisocyanate gave 2-(cis-3-{2-[1-(2-dimethylpropyl)-3-(4-fluorophenyl)ureido]ethoxy}cyclohexyloxymethyl)-6-methylbenzoic acid.

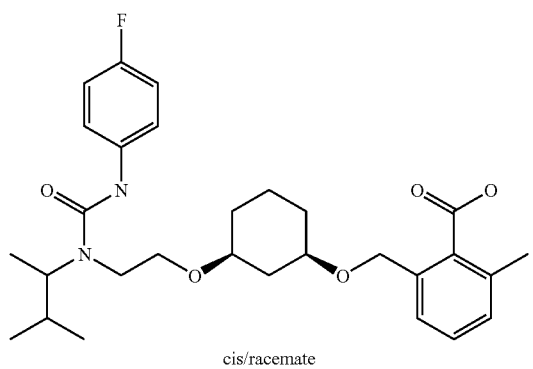

cis/racemate

C29H39FN2O5 (514.64), MS(ESI): 515 (M+H+).

EXAMPLE XLIII

Analogously to Example I, racemic methyl 2-methyl-6-[cis-3-(2-oxoethoxy)cyclohexyloxymethyl]benzoate, 1,2-dimethylpropylamine and butyl isocyanate gave 2-(cis-3-{2-[3-butyl-1-(2-dimethylpropyl)ureido]ethoxy}cyclohexyloxymethyl)-6-methylbenzoic acid.

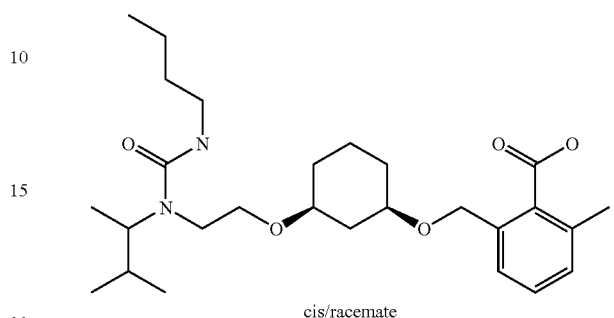

cis/racemate

C27H44N2O5 (476.66), MS(ESI): 477 (M+H+).

EXAMPLE XLIV

Analogously to Example I, racemic methyl 2-methyl-6-[cis-3-(2-oxoethoxy)cyclohexyloxymethyl]benzoate, cyclopropylamine and 2-methylphenyl isocyanate gave 2-{cis-3-[2-(1-cyclopropyl-3-o-tolylureido)ethoxy]cyclohexyloxymethyl}-6-methylbenzoic acid.

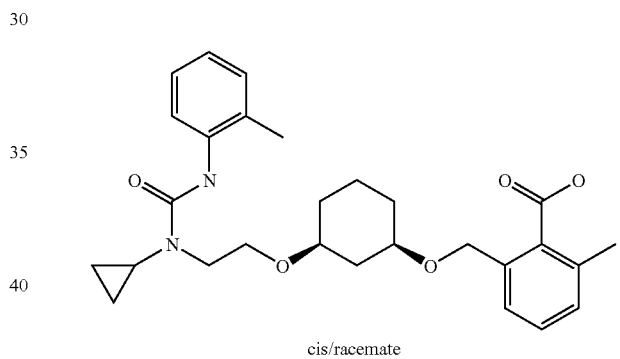

cis/racemate

C28H36N2O5 (480.61), MS(ESI): 481 (M+H+).

EXAMPLE XLV

Analogously to Example I, racemic methyl 2-methyl-6-[cis-3-(2-oxoethoxy)cyclohexyloxymethyl]benzoate, cyclopropylamine and 3-fluorophenyl isocyanate gave 2-(cis-3-{2-[1-cyclopropyl-3-(3-fluorophenyl)-ureido]ethoxy}cyclohexyloxymethyl)-6-methylbenzoic acid.

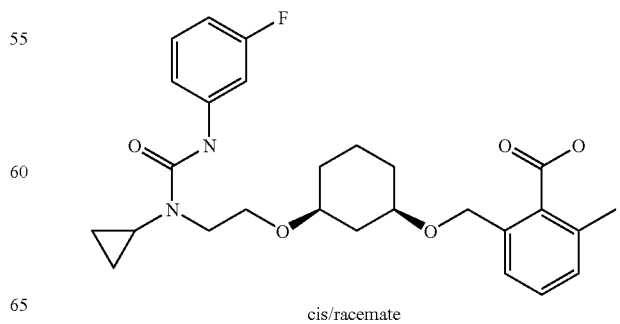

cis/racemate

C27H33FN2O5 (484.57), MS(ESI): 485 (M+H+).

EXAMPLE XLVI

Analogously to Example I, racemic methyl 2-methyl-6-[cis-3-(2-oxoethoxy)cyclohexyloxymethyl]benzoate, cyclopropylamine and 4-fluorophenyl isocyanate gave 2-(cis-3-{2-[1-cyclopropyl-3-(4-fluorophenyl)ureido]ethoxy}cyclohexyloxymethyl)-6-methylbenzoic acid.

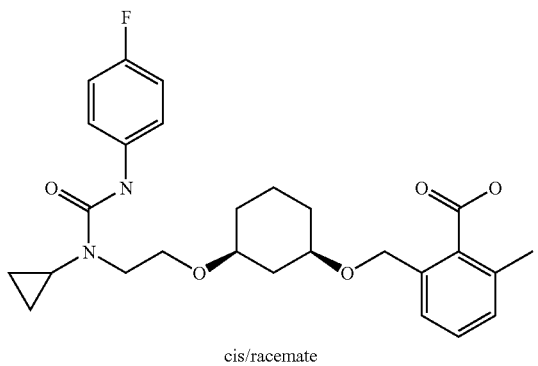

cis/racemate

C27H33FN2O5 (484.57), MS(ESI): 485 (M+H+).

EXAMPLE XLVII

Analogously to Example I, racemic methyl 2-methyl-6-[cis-3-(2-oxoethoxy)cyclohexyloxymethyl]benzoate, cyclopropylamine and butyl isocyanate gave 2-{cis-3-[2-(3-butyl-1-cyclopropylureido)ethoxy]cyclohexyloxymethyl}-6-methylbenzoic acid.

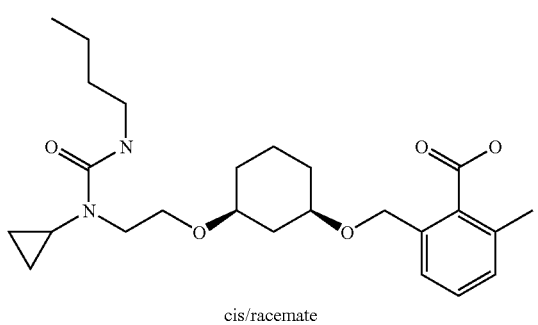

cis/racemate

C25H38N2O5 (446.59), MS(ESI): 447 (M+H+).

EXAMPLE XLVIII

Analogously to Example I, racemic methyl 2-methyl-6-[cis-3-(2-oxoethoxy)cyclohexyloxymethyl]benzoate, benzylamine and 2-methylphenylisocyanate gave 2-{cis-3-[2-(1-benzyl-3-o-tolylureido)ethoxy]-cyclohexyloxymethyl}-6-methylbenzoic acid.

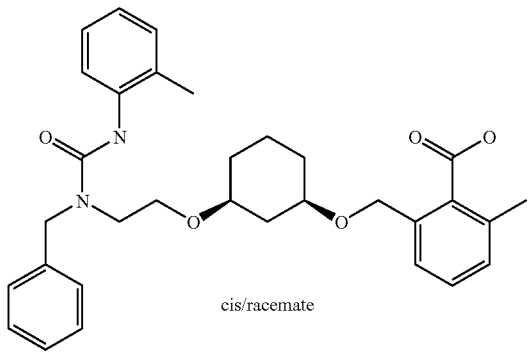

cis/racemate

C32H38N2O5 (530.67), MS(ESI): 531 (M+H+).

EXAMPLE XLIX

Analogously to Example I, racemic methyl 2-methyl-6-[cis-3-(2-oxoethoxy)cyclohexyloxymethyl]benzoate, benzylamine and 3-fluorophenyl isocyanate gave 2-(cis-3-{2-[1-benzyl-3-(3-fluorophenyl)ureido]ethoxy}-cyclohexyloxymethyl)-6-methylbenzoic acid.

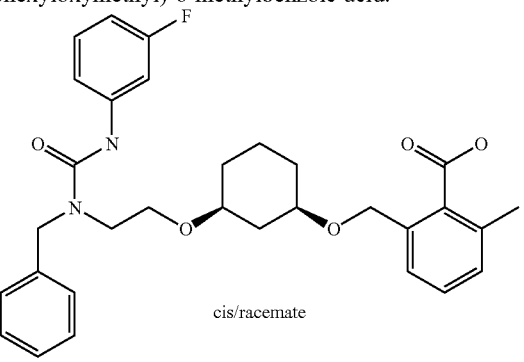

cis/racemate

C31H35FN2O5 (534.63), MS(ESI): 535 (M+H+).

EXAMPLE L

Analogously to Example I, racemic methyl 2-methyl-6-[cis-3-(2-oxoethoxy)cyclohexyloxymethyl]benzoate, benzylamine and 4-fluorophenyl isocyanate gave 2-(cis-3-{2-[1-benzyl-3-(4-fluorophenyl)ureido]ethoxy}-cyclohexyloxymethyl)-6-methylbenzoic acid.

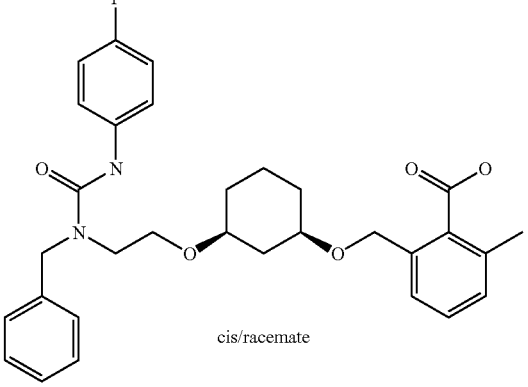

cis/racemate

C31H35FN2O5 (534.63), MS(ESI): 535 (M+H+).

EXAMPLE LI

Analogously to Example I, racemic methyl 2-methyl-6-[cis-3-(2-oxoethoxy)cyclohexyloxymethyl]benzoate, benzylamine and butyl isocyanate gave 2-{cis-3-[2-(1-benzyl-3-butylureido)ethoxy]cyclohexyloxymethyl}-6-methylbenzoic acid.

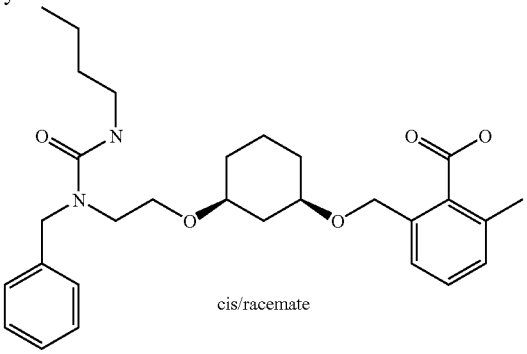

cis/racemate

C29H40N2O5 (496.65), MS(ESI): 497 (M+H+).

EXAMPLE LII

Analogously to Example I, racemic methyl 2-methyl-6-[cis-3-(2-oxoethoxy)cyclohexyloxymethyl]benzoate, pyridin-4-ylmethylamine and 2-methylphenyl isocyanate gave 2-methyl-6-{cis-3-[2-(1-pyridin-3-ylmethyl-3-o-tolylureido)ethoxy]cyclohexyloxymethyl}benzoic acid trifluoroacetate.

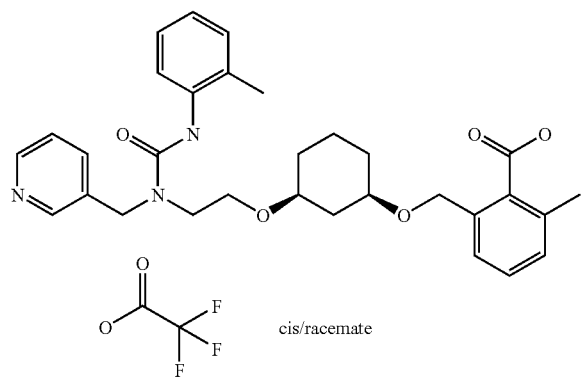

C31H37N3O5.C2HF3O2 (645.68), MS(ESI): 532 (M+H+).

EXAMPLE LIII

Analogously to Example I, racemic methyl 2-methyl-6-[cis-3-(2-oxoethoxy)cyclohexyloxymethyl]benzoate, pyridin-4-ylmethylamine and 3-fluorophenylisocyanate gave 2-(cis-3-{2-[3-(3-fluorophenyl )-1-pyridin-3-ylmethylureido]ethoxy}cyclohexyloxymethyl)-6-methylbenzoic acid trifluoroacetate.

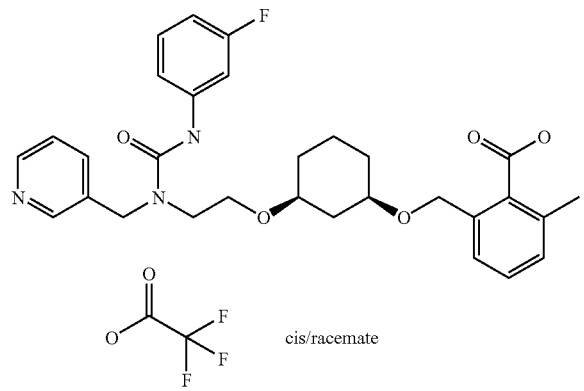

C30H35N3O5.C2HF23O2 (649.64), MS(ESI): 536 (M+H+).

EXAMPLE LIV

Analogously to Example I, racemic methyl 2-methyl-6-[cis-3-(2-oxoethoxy)cyclohexyloxymethyl]benzoate, pyridin-4-ylmethylamine and 4-fluorophenylisocyanate gave 2-(cis-3-{2-[3-(4-fluorophenyl)-1-pyridin-3-ylmethylureido]ethoxy}cyclohexyloxymethyl)-6-methylbenzoic acid trifluoroacetate.

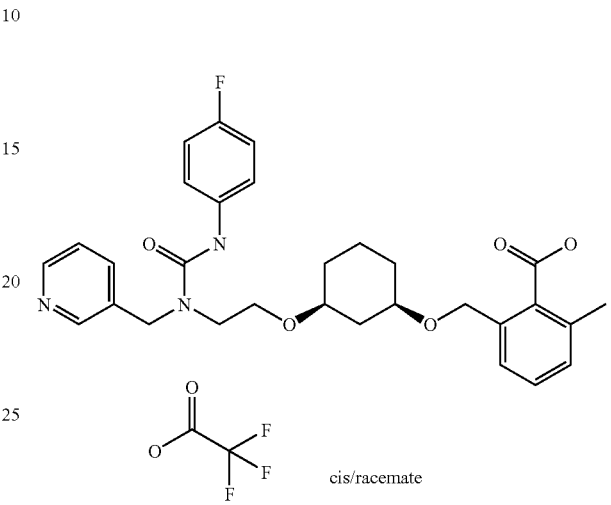

C30H34FN3O5.C2HF3O2 (649.64); MS(ESI): 536 (M+H+).

EXAMPLE LV

Analogously to Example I, racemic methyl 2-methyl-6-[cis-3-(2-oxoethoxy)cyclohexyloxymethyl]benzoate, pyridin-4-ylmethylamine and butyl isocyanate gave 2-{cis-3-[2-(3-butyl-1-pyridin-3-ylmethylureido)-ethoxy]cyclohexyloxymethyl}-6-methylbenzoic acid trifluoroacetate.

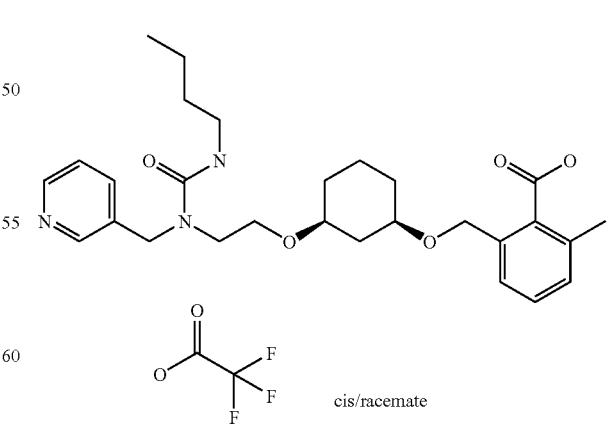

C28H39N3O5.C2HF3O2 (611.66), MS(ESI): 498 (M+H+).

EXAMPLE LVI

Analogously to Example I, racemic methyl 2-methyl-6-[cis-3-(2-oxoethoxy)cyclohexyloxymethyl]benzoate, 2-methylbutylamine and 3-fluorophenyl isocyanate gave 2-(cis-3-{2-[3-(3-fluorophenyl)-1-(2-methylbutyl)ureido]ethoxy}cyclohexyloxymethyl)-6-methylbenzoic acid.

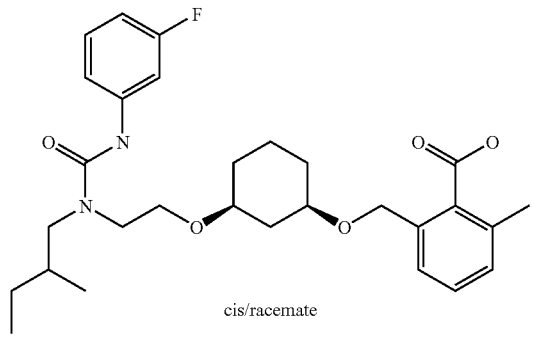

C29H39FN2O5 (514.643), MS(ESI): 515 (M+H+).

EXAMPLE LVII

Analogously to Example I, racemic methyl 2-methyl-6-[cis-3-(2-oxoethoxy)cyclohexyloxymethyl]benzoate, 2-methylbutylamine and 4-fluorophenyl isocyanate gave 2-(cis-3-{2-[3-(4-fluorophenyl)-1-(2-methylbutyl)ureido]ethoxy}cyclohexyloxymethyl)-6-methylbenzoic acid.

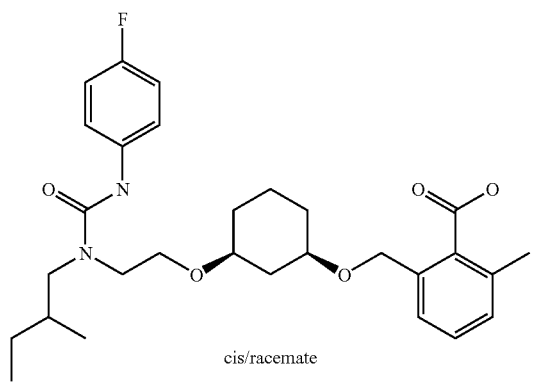

C29H39FN2O5 (514.64), MS(ESI): 515 (M+H+).

EXAMPLE LVIII

Analogously to Example I, racemic methyl 2-methyl-6-[cis-3-(2-oxoethoxy)cyclohexyloxymethyl]benzoate, cyclopentylamine and 2-methylphenyl isocyanate gave 2-{cis-3-[2-(1-cyclopentyl-3-o-tolylureido)ethoxy]cyclohexyloxymethyl}-6-methylbenzoic acid.

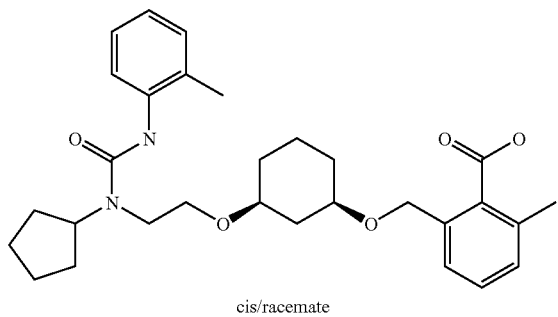

C30H40N2O5 (508.66), MS(ESI): 509 (M+H+).

EXAMPLE LIX

Analogously to Example I, racemic methyl 2-methyl-6-[cis-3-(2-oxoethoxy)cyclohexyloxymethyl]benzoate, cyclopentylamine and 3-fluorophenylisocyanate gave 2-(cis-3-{2-[1-cyclopentyl-3-(3-fluorophenyl)ureido]ethoxy}cyclohexyloxymethyl)-6-methylbenzoic acid.

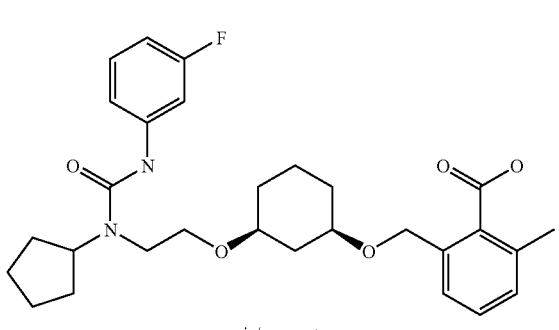

C29H37FN2O5 (512.62), MS(ESI): 513 (M+H+).

EXAMPLE LX

Analogously to Example I, racemic methyl 2-methyl-6-[cis-3-(2-oxoethoxy)cyclohexyloxymethyl]benzoate, cyclopentylamine and 4-fluorophenyl isocyanate gave 2-(cis-3-{2-[1-cyclopentyl-3-(4-fluorophenyl)ureido]ethoxy}cyclohexyloxymethyl)-6-methylbenzoic acid.

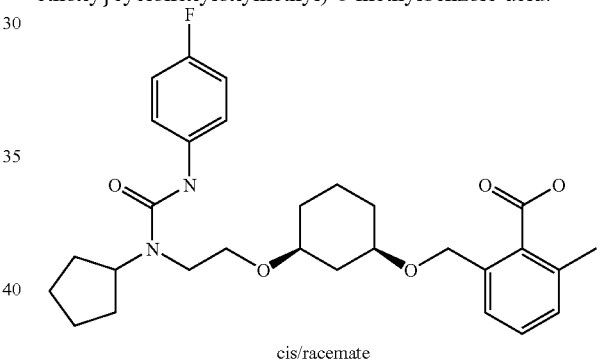

C29H37FN2O5 (512.62), MS(ESI): 513 (M+H+).

EXAMPLE LXI

Analogously to Example I, racemic methyl 2-methyl-6-[cis-3-(2-oxoethoxy)cyclohexyloxymethyl]benzoate, cyclopentylamine and butyl isocyanate gave 2-{cis-3-[2-(3-butyl-1-cyclopentylureido)ethoxy]cyclohexyloxymethyl}-6-methylbenzoic acid.

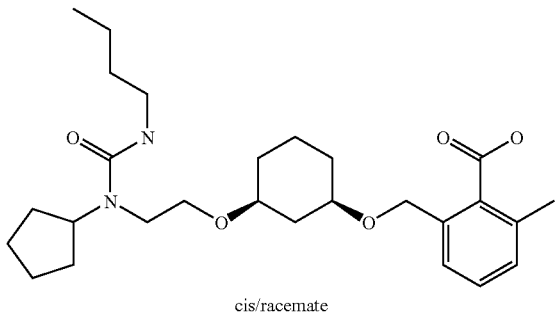

C27H42N2O5 (474.65), MS(ESI): 475 (M+H+).

EXAMPLE LXII

Analogously to Example I, racemic methyl 2-methyl-6-[cis-3-(2-oxoethoxy)cyclohexyloxymethyl]benzoate, 2-chlorobenzylamine and benzoyl chloride gave 2-(cis-3-{2-[benzoyl-(2-chlorobenzyl)amino]ethoxy}-cyclohexyloxymethyl)-6-methylbenzoic acid.

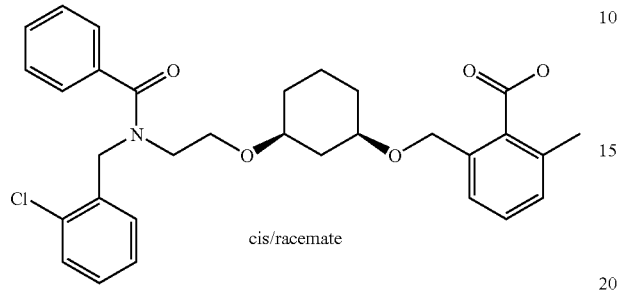

cis/racemate $C_{31}H_{34}ClNO_5$ (536.07), MS(ESI): 536 (M+H+).

R is NR1R2 or OR1;
R1, R2 are each independently H, (C1-C6)-alkyl, (C3-C8)-cycloalkyl or (C6-C10)-aryl, wherein said (C6-C10)-aryl is optionally substituted by F, Cl or (C1-C4)-alkyl;
R3 is (C3-C6)-cycloalkyl or (C1-C10)-alkyl, wherein each group is optionally substituted by phenyl, pyridyl, morpholinyl or (C3-C6)-cycloalkyl, and wherein said phenyl substituent is optionally substituted by chlorine or (C1-C4)-alkyl;
X is (C1-C6)-alkanediyl, wherein one or more carbon atoms therein are optionally replaced by oxygen atoms;
Y is (C1-C6)-alkanediyl, wherein one or more carbon atoms therein are optionally replaced by oxygen atoms;
R4 is H or (C1-C4)-alkyl;
R5 is (C1-C4)-alkyl;
and pharmaceutically acceptable salts thereof.

2. The compound of claim 1 wherein:
ring A is (C3-C8)-cycloalkane-1,3-diyl or (C3-C8)-cycloalkene-1,3-diyl;
R is NR1R2;

---

---

We claim:
1. A compound of the formula I

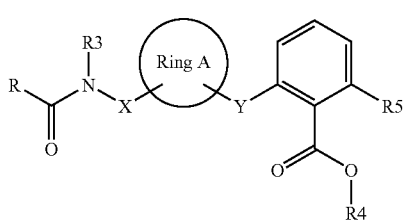

wherein
ring A is (C3-C8)-cycloalkanediyl or (C3-C8)-cycloalkenediyl;
R1, R2 are each independently H, (C1-C6)-alkyl, (C3-C8)-cycloalkyl or (C6-C10)-aryl, wherein said (C6-C10)-aryl group is optionally substituted by F, Cl or (C1-C4)-alkyl;
R3 is (C3-C6)-cycloalkyl or (C1-C8)-alkyl, wherein each group is optionally substituted by phenyl, pyridyl, morpholinyl, (C3-C6)-cycloalkyl, and wherein said phenyl substituent is optionally substituted by chlorine or methyl;
X is (C1-C3)-alkanediyl, wherein one carbon atom therein is optionally replaced by an oxygen atom;
Y is (C1-C3)-alkanediyl, wherein the carbon atom adjacent to ring A in said (C1-C3)-alkanediyl group is optionally replaced by an oxygen atom;
R4 is H;
R5 is methyl;
and pharmaceutically acceptable salts thereof.

3. The compound of claim 2 wherein:
ring A is cyclohexane-1,3-diyl;
R is NR1R2;
R1 is H;
R2 is (C1-C6)-alkyl, cyclohexyl or phenyl, wherein said phenyl group is optionally substituted by F, Cl or (C1-C4)-alkyl;
R3 is (C3-C6)-cycloalkyl or (C1-C8)-alkyl, each of which is optionally substituted by phenyl, pyridyl, morpholinyl, cyclopropyl, cyclopentyl, cyclohexyl, and wherein said phenyl substituent is optionally substituted by chlorine or methyl;
X is O—CH$_2$—CH$_2$;
Y is OCH$_2$;
R4 is H;
R5 is methyl;
and pharmaceutically acceptable salts thereof.

4. The compound of claim 3 wherein:
ring A is cyclohexane-1,3-diyl;
R is NR1R2;
R1 is H;
R2 is (C1-C4)-alkyl, cyclohexyl or phenyl, wherein said phenyl group is optionally substituted by F, Cl or methyl;
R3 is (C3-C6)-cycloalkyl or (C1-C8)-alkyl, each of which is optionally substituted by phenyl, pyridyl, morpholinyl, cyclopropyl, cyclopentyl or cyclohexyl, and wherein said phenyl substituent is optionally substituted by chlorine or methyl;
X is O—CH$_2$—CH$_2$;
Y is OCH$_2$;
R4 is H;
R5 is methyl;
and pharmaceutically acceptable salts thereof.

5. The compound of claim 4 wherein the link of X and Y to ring A is cis-configured.

6. A pharmaceutical composition comprising a pharmaceutically acceptable carrier and one or more compounds of claim 1.

7. The pharmaceutical composition of claim 6 further comprising at least one additional ingredient.

8. The pharmaceutical composition of claim 7 wherein said additional active ingredient has favorable effects on metabolic disturbances or disorders.

9. The pharmaceutical composition of claim 7 wherein said additional active ingredient is an antidiabetic.

10. The pharmaceutical composition of claim 7 wherein said additional active ingredient is a lipid modulator.

11. A method of treating disorders of insulin resistance comprising administering to a patient in need thereof a therapeutically effective amount of a compound of claim 1.

12. A method of treating diabetes mellitus and squelae associated therewith comprising administering to a patient in need thereof a therapeutically affective amount of compound of formula 1.

13. A method of treating dyslipidemia and squelae associated therewith comprising administering to a patient in need thereof a therapeutically effective amount of a compound of claim 1.

14. A method of treating disorders of fatty acid metabolism and glucose utilization comprising administering to a patient in need thereof a therapeutically effective amount of a compound of claim 1 in combination with at least one further active compound.

15. A method of treating disorders of insulin resistance comprising administering to a patient in need thereof a therapeutically effective amount of a compound of claim 1 in combination with at least one further active compound.

* * * * *